(12) United States Patent
Sharma et al.

(10) Patent No.: US 9,181,212 B2
(45) Date of Patent: Nov. 10, 2015

(54) METHOD OF PRODUCING BERAPROST

(71) Applicant: Lung Biotechnology PBC, Silver Spring, MD (US)

(72) Inventors: Vijay Sharma, Olney, MD (US); Hitesh Batra, Herndon, VA (US); Sudersan Tuladhar, Silver Spring, MD (US)

(73) Assignee: Lung Biotechnology PBC, Silver Spring, MD (US)

( * ) Notice: Subject to any disclaimer, the term of this patent is extended or adjusted under 35 U.S.C. 154(b) by 0 days.

(21) Appl. No.: 14/294,384

(22) Filed: Jun. 3, 2014

(65) Prior Publication Data

US 2014/0275573 A1    Sep. 18, 2014

Related U.S. Application Data

(62) Division of application No. 13/524,568, filed on Jun. 15, 2012, now Pat. No. 8,779,170.

(60) Provisional application No. 61/497,754, filed on Jun. 16, 2011.

(51) Int. Cl.
| | |
|---|---|
| *C07D 307/93* | (2006.01) |
| *C07C 259/06* | (2006.01) |
| *C07F 7/18* | (2006.01) |
| *C07F 9/28* | (2006.01) |
| *C07F 9/40* | (2006.01) |

(52) U.S. Cl.
CPC ............ *C07D 307/93* (2013.01); *C07C 259/06* (2013.01); *C07F 7/1844* (2013.01); *C07F 7/1892* (2013.01); *C07F 9/28* (2013.01); *C07F 9/4006* (2013.01)

(58) Field of Classification Search
CPC .................................................. C07D 307/93
USPC ................................................ 549/214, 458
See application file for complete search history.

(56) References Cited

U.S. PATENT DOCUMENTS

| 4,076,947 A | 2/1978 | Schaub et al. |
| 4,424,376 A | 1/1984 | Moniot et al. |
| 4,880,939 A | 11/1989 | Ohno et al. |
| 5,202,447 A | 4/1993 | Ohno et al. |
| 7,345,181 B2 | 3/2008 | Kim et al. |
| 7,858,831 B2 | 12/2010 | Meyer et al. |

OTHER PUBLICATIONS

Zhao Dishun, "Principles and Applications of Fine Organic Synthesis," Chemistry Postgraduate Textbook, Mar. 2009, 197-209, with English translation.
Heung Bae Jeon et al., "New A-ring analogs of the hormone 1α,25-dihydroxyvitamin $D_3$: (2'-hydroxymethyl)tetrahydrofuro[1,2-α]-25-hydroxyvitamin $D_3$," Tetrahedron, 2009 (online Dec. 24, 2008), 7(65):1235-1240.
Bergman et al., "A Facile Synthesis of 1,4-diketones," Tetrahedron Letters, 1990, 31(19):2783-2786.
Kramp et al., "Fully Stereocontrolled Total Synthesis of the Prostacyclin Analogues 16S-Iloprost and 16S-3-Oxa-Iloprost by a Common Route, Using Alkenylcopper-Azoalkene Conjugate Addition, Asymmetric Olefination, and Allylic Alkylation," J. Am. Chem. Society, 2005, 127:17910-17920.
Nilson et al., "Total Synthesis of (−)-Nakadomarin A," Organic Letters, 2010, 12(21):4912-4915.
Wakita et al., "Total Synthesis of Optically Active m-Phenylene $PGI_2$ Derivative: Beraprost," Heterocycles, 2000, 53(5):1085-1110.
Zuercher et al., "Ruthenium-Catalyzed Polycyclization Reactions," J. Org. Chem., 1998, 63:4291-4298.
Nagase et al,. "Synthesis of (+)-5,6,7-Trinor-4,8-Inter-*m*-Phenylene $PGI_2^{1)}$," Tetrahedron Letters, 1990, 31(31):4493-4494.
Reddy et al., "Formal Synthesis of Antiplatelet Drug, Beraprost," Organic Letters, 2012 (published online Dec. 14, 2011), 14(1):299-301.
Wakita et al., "Regioselective protection of 11-hydroxy group and inversion of configuration at C-15 in *m*-phenylene $PGI_2$ derivatives," Heterocycles, 1998, 48(12):2559-2571.

*Primary Examiner* — Niloofar Rahmani
(74) *Attorney, Agent, or Firm* — Foley & Lardner LLP

(57) ABSTRACT

An improved method is described for making single isomers of synthetic benzoprostacyclin analog compounds, in particular the pharmacologically active 314-d isomer of beraprost. In contrast to the prior art, the method is stereoselective and requires fewer steps than the known methods for making these compounds.

12 Claims, 4 Drawing Sheets

METHOD OF PRODUCING BERAPROST

CROSS-REFERENCE TO RELATED APPLICATIONS

This application is a Divisional of U.S. application Ser. No. 13/524,568, filed Jun. 15, 2012, which claims priority from U.S. Provisional Application No. 61/497,754, filed Jun. 16, 2011, the entirety of which is incorporated herein by reference.

FIELD

The present application relates to a process for selectively producing single-isomer benzoprostacyclin derivatives including beraprost and its derivatives. The present invention also relates to a novel process for attaching the alpha side-chain to single-isomer key intermediate leading to beraprost and related derivatives.

BACKGROUND OF THE INVENTION

Prostacyclin derivatives are useful pharmaceutical compounds possessing activities such as platelet aggregation inhibition, gastric secretion reduction, lesion inhibition, and bronchodilation. Beraprost is a synthetic benzoprostacyclin analogue of natural prostacyclin that is currently under clinical trials for the treatment of pulmonary hypertension and vascular disease (excluding renal disease) in North America and Europe.

Beraprost and related benzoprostacyclin analogues of the formula (I) are disclosed in U.S. Pat. No. 5,202,447 and Tetrahedron Lett. 31, 4493 (1990). Furthermore, as described in U.S. Pat. No. 7,345,181, several synthetic methods are known to produce benzoprostacyclin analogues.

Known synthetic methods generally require one or more resolutions of intermediates to obtain the pharmacologically active isomer of beraprost or a related benzoprostacyclin analogue. Also, current pharmaceutical formulations of beraprost or a related benzoprostacyclin analogues may consist of several isomers of the pharmaceutical compound, and only one of which is primarily responsible for the pharmacologic activity of the drug. Isolation of the pharmaceutically active isomer of beraprost compounds from current synthetic methods requires multiple preparative HPLC or chromatographic purification procedures or multiple recrystallizations that are not amenable to a commercially applicable scale. Therefore, it is desired to achieve an efficient, commercially applicable synthetic route to the active isomer of beraprost or a related benzoprostacyclin analogue.

SUMMARY OF THE INVENTION

An object of the present invention is to provide a method which can produce the pharmaceutical compound represented by the general formula (I) in a substantially isomerically pure form, in fewer steps than the prior art and in commercially useful quantities. Another object of the present invention is to provide a method which can produce the tricyclic intermediates represented by the general formula (IV) and (V) in a substantially isomerically pure form which can be used for the production of pharmaceutical compounds represented by the general formula (I) or other similar compounds. Yet another object of the current invention is to provide a novel method which can attach the alpha side-chain to single-isomer key intermediate leading to the pharmaceutical compound represented by the general formula (I). This invention also claims the preparation of compound (VII) where 6, 2a=H, also referred to as the diol single-isomer exclusively in 95-100% purity, which can be transformed into beraprost and related derivatives of the general formula (I).

One embodiment provides for a process for preparing a compound of the following formula:

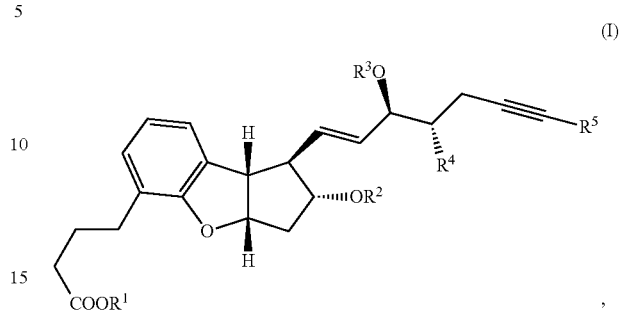

(I)

wherein $R^1$ represents a cation, H, or $C_{1-12}$ alkyl, $R^2$ and $R^3$ each represent H or a hydroxy protective group, $R^4$ represents H or $C_{1-3}$ alkyl, and $R^5$ represents H or $C_{1-6}$ alkyl, comprising the steps of:

(1) performing a cycloaddition reaction on the compound of the following formula:

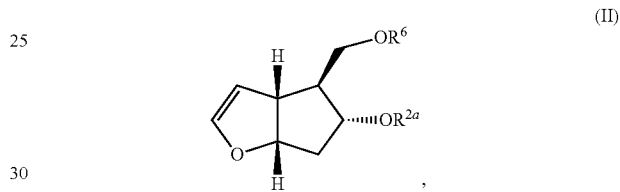

(II)

wherein in $R^{2a}$ and $R^6$ independently represent hydroxy protecting groups, with a compound of the following formula:

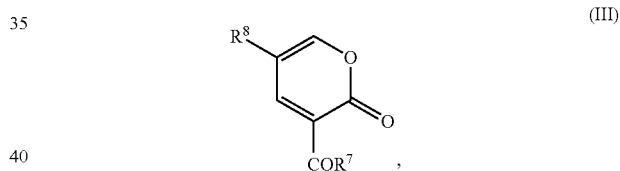

(III)

wherein $R^7$ represents $C_{1-6}$ alkoxy or $C_{1-12}$ alkyl-$COOR^9$, where $R^9$ represents $C_{1-3}$ alkyl and $R^8$ represents halide or H to form a compound of the following formula:

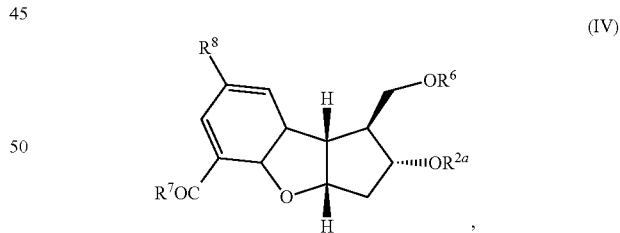

(IV)

wherein $R^{2a}$, $R^6$, $R^7$, and $R^8$ are each defined above;

(2) aromatizing the cyclodiene of formula (IV) to form the aromatic product of the following formula:

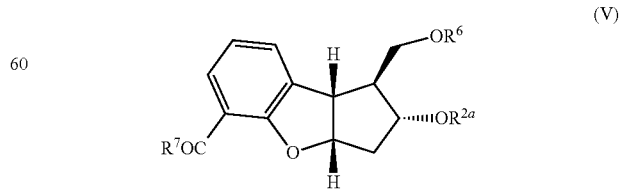

(V)

(3) Reducing the ester of the compound of formula (V) to a benzyl alcohol and oxidation of benzyl alcohol to an aldehyde followed by addition of a carbon to said aldehyde to form an alkyne resulting in a compound of the following formula:

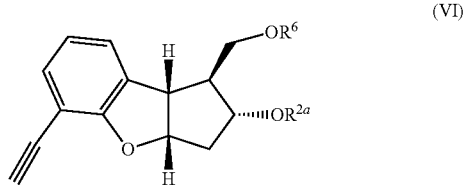
(VI)

(4) coupling the terminal alkyne with $N_2CH_2CO_2R^{1a}$, wherein $R^{1a}$ represents a $C_{1-12}$ alkyl followed by hydrogenation of the alkyne to its corresponding alkane to form a compound of the following formula:

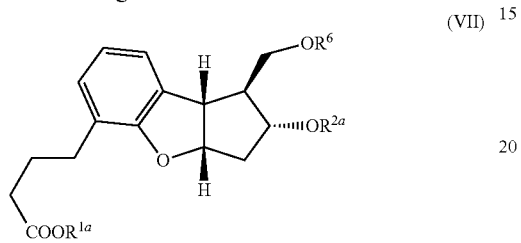
(VII)

(5) selectively deprotecting the primary hydroxyl protective group, followed by oxidation of the primary hydroxyl group to the corresponding aldehyde, followed by coupling with a side-chain of the formula:

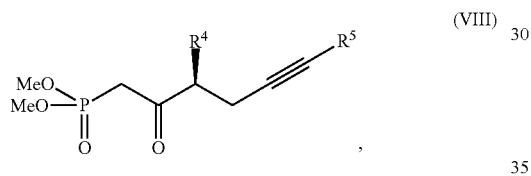
(VIII)

wherein $R^4$ and $R^5$ are each defined above to form a compound of the following formula:

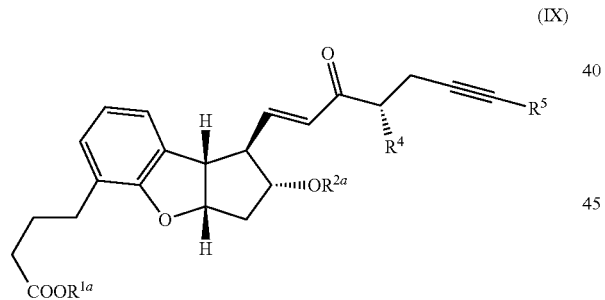
(IX)

(6) reduction of the ketone, deprotection of any remaining hydroxy protective group and optionally converting the $R^{1a}$ into a cation or H to form a compound of the following formula:

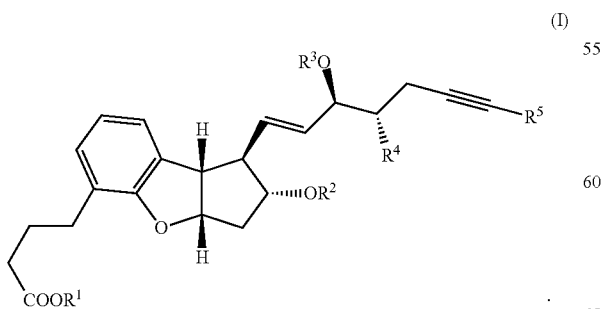
(I)

In another embodiment, the compound of formula (I) is produced as a substantially pure single isomer. In another embodiment, $R^1$ is a cation or H, $R^2$ and $R^3$ are H, $R^4$ and $R^5$ are $CH_3$. In another embodiment, $R^2$, $R^3$, $R^{2a}$ and $R^6$ each independently represent trimethylsilyl, triethylsilyl, t-butyldimethylsilyl, t-butyldiphenylsilyl, phenyldimethylsilyl, or tetrahydropyranyl. In another embodiment, the cycloaddition of step (1) is an inverse electron demand Diels Alder reaction followed by thermal decarboxylation. In another embodiment, the aromatization step (2) is treatment of the compound of formula (IV) with palladium on carbon.

Another embodiment provides for a process of for preparing the stereoselectively produced isomeric compound of the following formula:

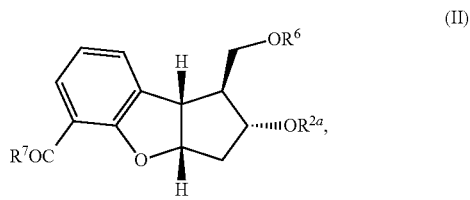
(II)

wherein in $R^{2a}$ and $R^6$ independently represent hydroxy protecting groups and $R^7$ represents $C_{1-6}$ alkoxy or $C_{1-12}$ alkyl-$COOR^9$, where $R^9$ represents $C_{1-3}$ alkyl comprising the steps of:

(1) performing a cycloaddition reaction on the compound of the following formula:

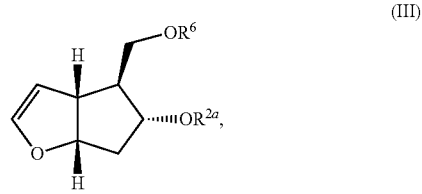
(III)

wherein in $R^{2a}$ and $R^6$ independently represent hydroxy protecting groups to form a compound of the following formula:

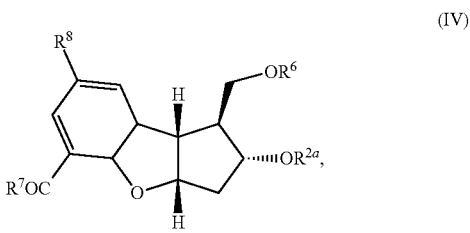
(IV)

wherein $R^{2a}$, $R^6$ and $R^7$ are each defined above;
(2) aromatization of the cyclodiene of formula (IV) to form the aromatic product of the following formula:

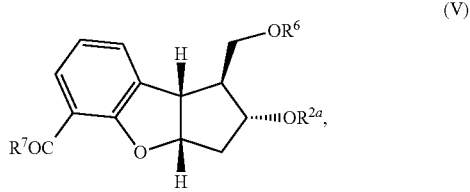
(V)

wherein $R^{2a}$, $R^6$ and $R^7$ are each defined above. In one embodiment, $R^{2a}$ and $R^6$ each independently represent trimethylsilyl, triethylsilyl, t-butyldimethylsilyl, t-butyldiphenylsilyl, phenyldimethylsilyl, or tetrahydropyranyl. In another embodiment, the cycloaddition of step (1) is an inverse electron demand Diels Alder reaction followed by thermal decarboxylation. In another embodiment, the aromatization step (2) is treatment of the compound of formula (IV) with palladium on carbon. Another embodiment provides a process for preparing a compound of the following formula:

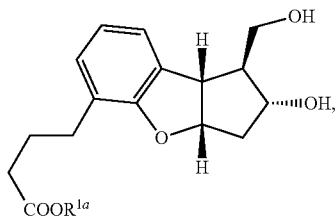
(VII)

wherein $R^{1a}$ represents a cation, H, or $C_{1-12}$ alkyl, comprising the steps of:
(1) performing a cycloaddition reaction on the compound of the following formula:

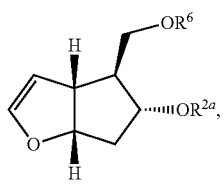
(II)

wherein in $R^{2a}$ and $R^6$ independently represent hydroxy protecting groups, with a compound of the following formula:

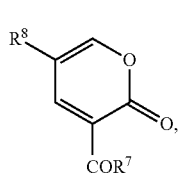
(III)

wherein $R^7$ represents $C_{1-6}$ alkoxy or $C_{1-12}$ alkyl-$COOR^9$, where $R^9$ represents $C_{1-3}$ alkyl and $R^8$ represents halide or H to form a compound of the following formula:

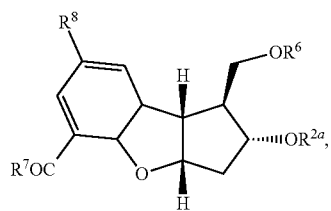
(IV)

wherein $R^{2a}$, $R^6$, $R^7$, and $R^8$ are each defined above;
(2) aromatizing the cyclodiene of formula (IV) to form the aromatic product of the following formula:

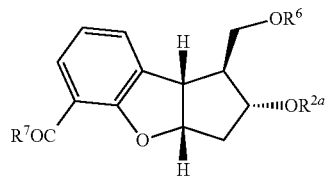
(V)

(3) Reducing the ester of the compound of formula (V) to a benzyl alcohol and oxidation of benzyl alcohol to an aldehyde followed by addition of a carbon to said aldehyde to form an alkyne resulting in a compound of the following formula:

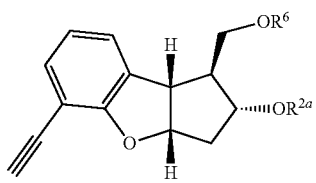
(VI)

(4) coupling the terminal alkyne with $N_2CH_2CO_2R^{1a}$, wherein $R^{1a}$ represents a $C_{1-12}$ alkyl followed by hydrogenation of the alkyne to its corresponding alkane followed by deprotection of the hydroxyl protective groups to form a compound of the following formula:

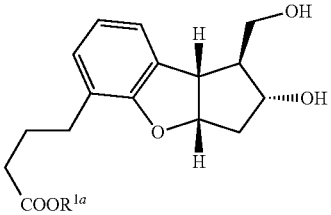
(VII)

wherein $R^{1a}$ represents a cation, H, or $C_{1-12}$ alkyl. In another embodiment, the compound of formula (VII) is produced as a substantially pure single isomer.

Another embodiment provides for compounds represented by the formula:

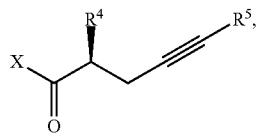

wherein x is

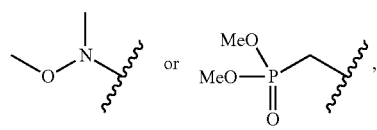

$R^4$ represents H or $C_{1-3}$ alkyl, and
$R^5$ represents H or $C_{1-6}$ alkyl, and the compound has a chiral purity of at least 95%.
Additional embodiments provide a chiral purity of at least 95%, 97%, 99%, or greater than 99%. Another embodiment provides $R^4$ and $R^5$ are each $CH_3$.

Another embodiment provides for a process for preparing a substantially pure compound of the following formula:

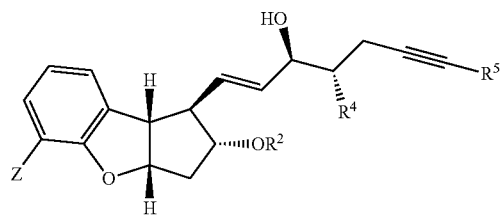

wherein
$R^2$ represents H or a hydroxy protective group,
$R^4$ represents H or $C_{1-3}$ alkyl,
$R^5$ represents H or $C_{1-6}$ alkyl, and
Z represents $C_{1-12}$ alkyl-$COOR^{12}$, $R^{12}$ is a cation, H, or $C_{1-12}$ alkyl, comprising the steps of:

(1) reacting an aldehyde of the formula

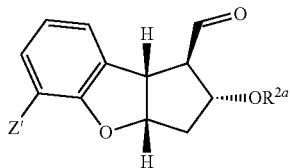

with a substantially pure compound of the formula:

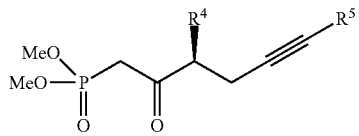

wherein Z' is $C_{1-12}$ alkyl-$COOR^{12'}$, $R^{12'}$ is a $C_{1-6}$ alkyl or a protecting group, $R^{2a}$ is a hydroxy protecting group, $R^4$ and $R^5$ are each defined above to form a compound of the following formula:

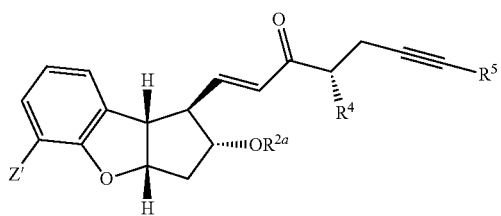

(2) selectively reducing the carbonyl and deprotecting secondary alcohol to form a substantially pure compound of the following formula:

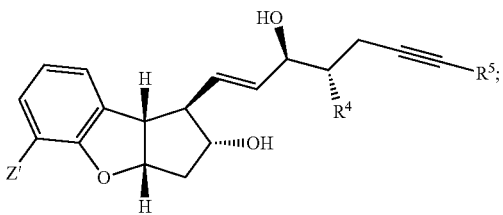

and
(3) optionally deprotecting the ester of protected acid of Z' to form an acid or salt thereof. In one embodiment, the selective reduction of the carbonyl includes an asymmetric catalyst. In one embodiment, the step 3 is not optional, and Z' is $C_{1-12}$ alkyl-$COOR^{12'}$, and $R^{12'}$ is a $C_{1-6}$ alkyl. In one embodiment, the step 3 is not optional, and $R^4$ and $R^5$ are each $CH_3$, Z is $(CH_2)_3COOR^{12}$ and $R^{12}$ is a cation or H. In one embodiment, $R^{12}$ is a cation and the cation is $K^+$. In one embodiment, the resulting substantially pure compound comprises greater than 99% of the isomer represented by the following formula:

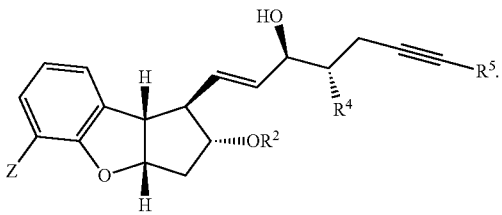

DETAILED DESCRIPTION OF THE PREFERRED EMBODIMENTS

Figure 1:
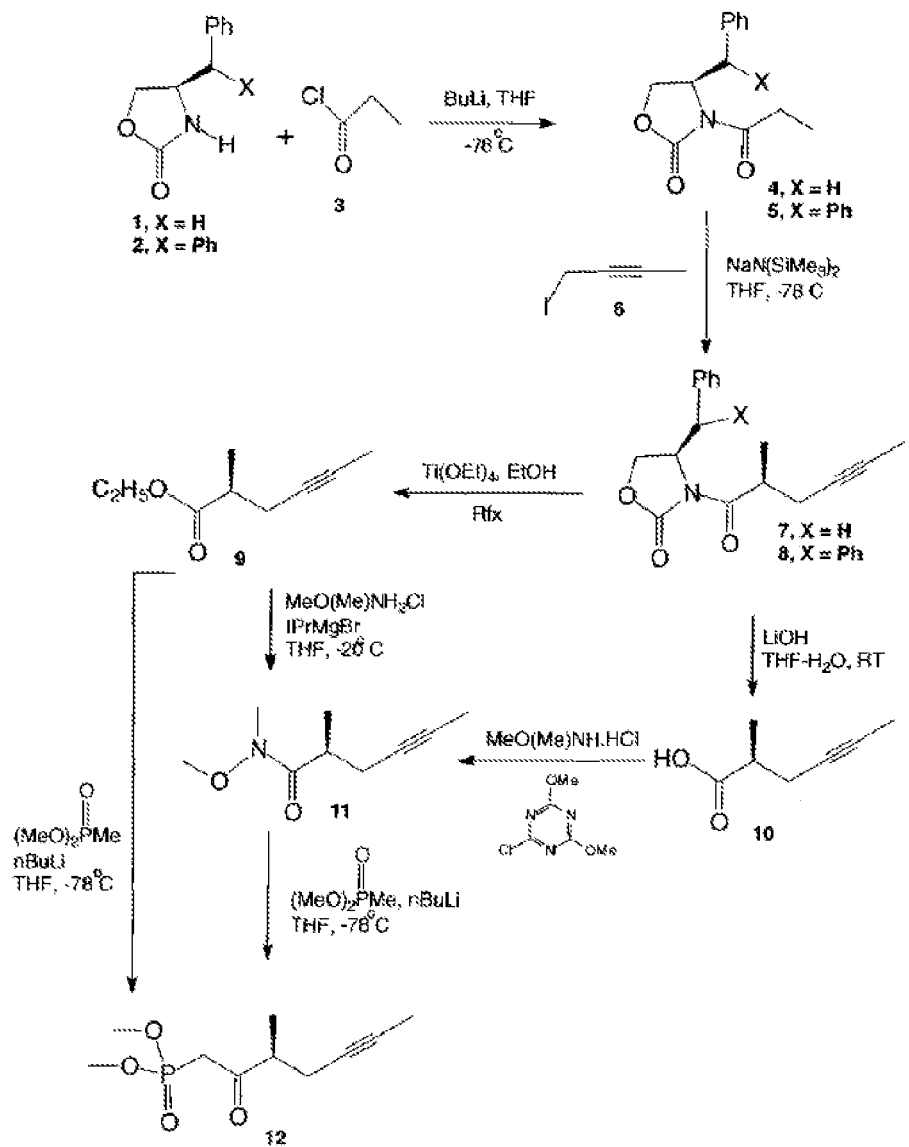
FIG. 1 shows an embodiment of the synthesis of the side chain compound for coupling to the core beraprost analogue.
Figure 2:
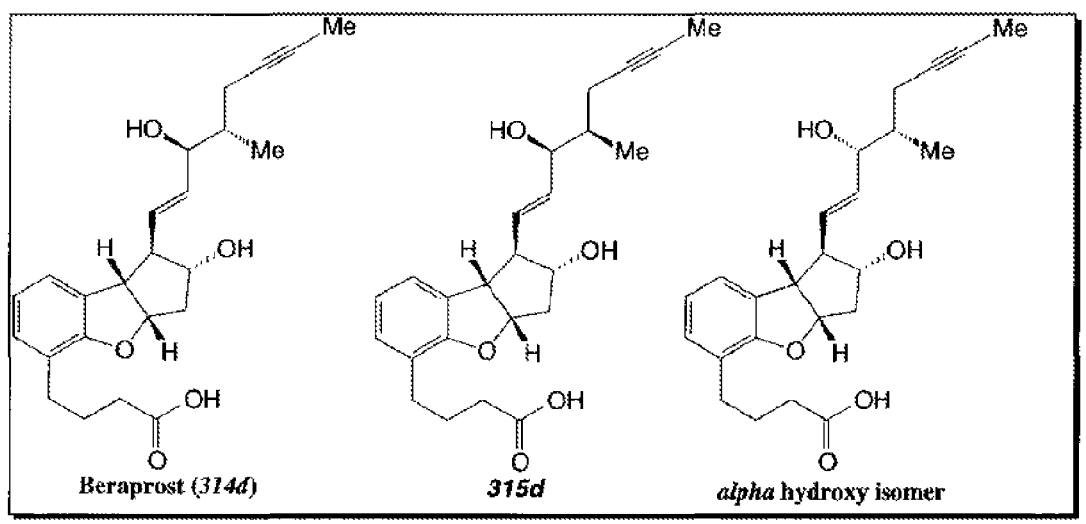
FIG. 2 shows Beraprost 314d and its isomers
Figure 3:
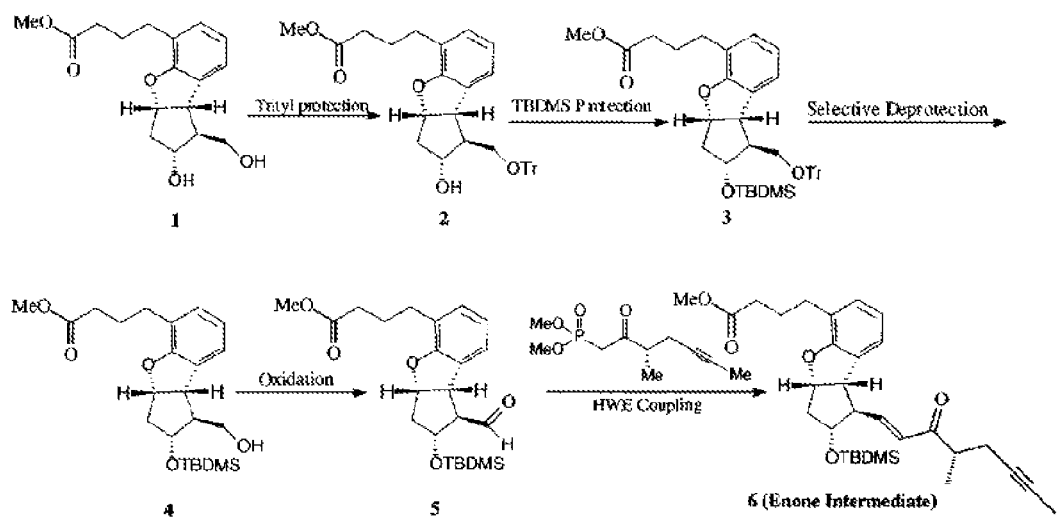
FIG. 3 shows an embodiment of selective protection strategy leading to an enone intermediate
Figure 4:
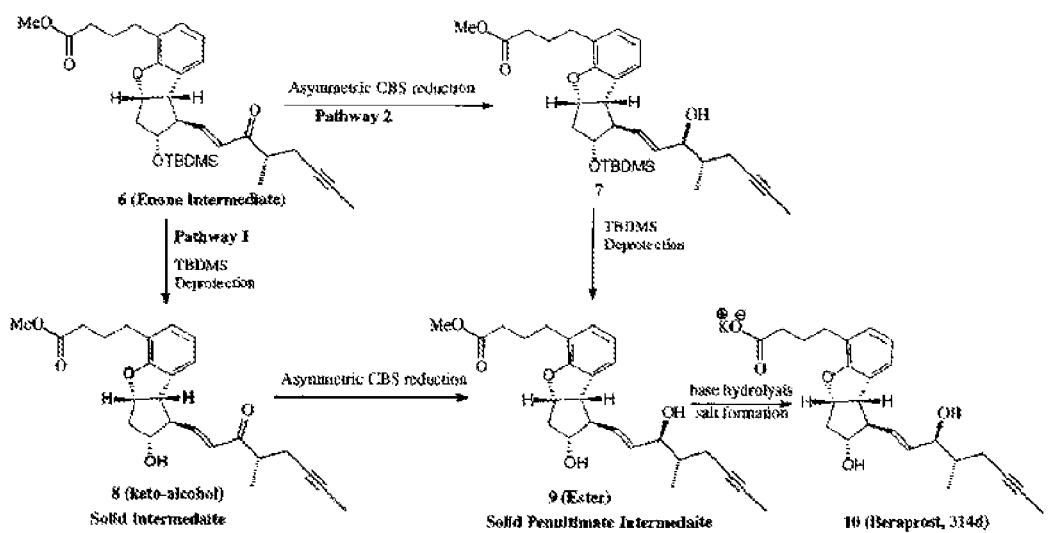
FIG. 4 shows an embodiment of the asymmetric synthesis of Beraprost from an enone intermediate.

All references cited herein are incorporated by reference in their entirety.

Various inventions and/or their embodiments disclosed herein relate to methods of synthesizing a substantially pure isomer of beraprost or its related derivatives. In one preferred embodiment, the substantially pure isomer of beraprost is represented by the formula (I). In another preferred embodiment, the substantially pure isomer of beraprost is Beraprost (314d) or a related analogue, such as a salt, solvate or prodrug thereof. Other embodiments include compounds that are novel intermediates of one or more of the synthetic routes disclosed herein.

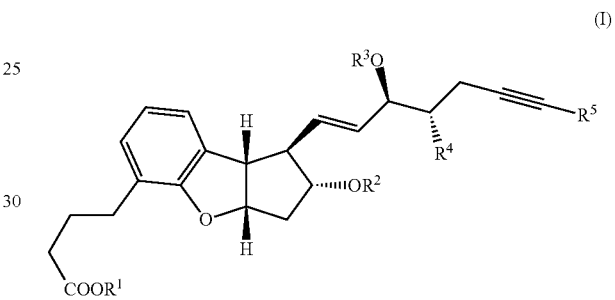

(I)

wherein $R^1$ represents a cation, H, or $C_{1-12}$ alkyl, $R^2$ and $R^3$ each represent H or a hydroxy protective group, $R^4$ represents H or $C_{1-3}$ alkyl, and $R^5$ represents H or $C_{1-6}$ alkyl.

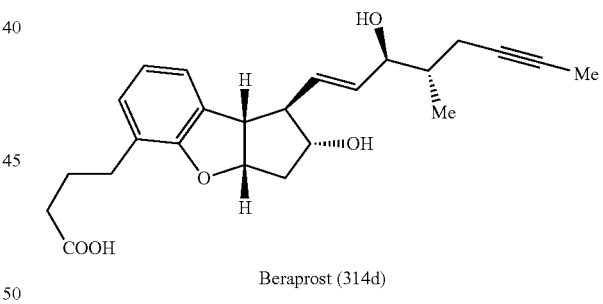

Beraprost (314d)

Unless otherwise specified, "a" or "an" means "one or more" throughout this specification and claims.

The term "or" as used herein means "and/or" unless specified other wise.

Important synthetic methods which can be used as appropriate herein to prepare compounds are generally known in the art and are described in, for example, *March's Advanced Organic Chemistry*, 6th Ed., 2007; T. W. Greene, *Protective Groups in Organic Synthesis*, John Wiley and Sons, 1991.

When referring to a moiety (e.g. a compound) in singular, the plural is meant to be included. Thus, when referring to a specific moiety, e.g. "compound", this means "at least one" of that moiety, e.g. "at least one compound", unless specified otherwise.

As used herein, "halo" or "halogen" or even "halide" can refer to fluoro, chloro, bromo, and iodo.

As used herein, "alkyl" can refer to a straight-chain, branched, or cyclic saturated hydrocarbon group. Examples of alkyl groups include methyl (Me), ethyl (Et), propyl (e.g., n-propyl and iso-propyl), butyl (e.g., n-butyl, iso-butyl, sec-butyl, tert-butyl), pentyl groups (e.g., n-pentyl, iso-pentyl, neopentyl), and the like. In various embodiments, an alkyl group can have 1 to 30 carbon atoms, for example, 1-20 carbon atoms (i.e., $C_1$-$C_{20}$ alkyl group). In some embodiments, an alkyl group can have 1 to 6 carbon atoms, and can be referred to as a "lower alkyl group." Examples of lower alkyl groups include methyl, ethyl, propyl (e.g., n-propyl and iso-propyl), and butyl groups (e.g., n-butyl, iso-butyl, sec-butyl, tert-butyl). In some embodiments, alkyl groups can be substituted as defined herein. In some embodiments, substituted, saturated hydrocarbons, C1-C6 mono- and di- and prehalogen substituted saturated hydrocarbons and amino-substituted hydrocarbons are preferred, with perfluoromethyl, perchloromethyl, perfluoro-tert-butyl, and perchloro-tert-butyl being the most preferred. The term "substituted alkyl" means any unbranched or branched, substituted saturated hydrocarbon, with unbranched C1-C6 alkyl secondary amines, substituted C1-C6 secondary alkyl amines, and unbranched C1-C6 alkyl tertiary amines being within the definition of "substituted alkyl," but not preferred. In some embodiments, the term "alkyl" means any unbranched or branched, substituted saturated hydrocarbon. In some embodiments, cyclic compounds, both cyclic hydrocarbons and cyclic compounds having heteroatoms, are within the meaning of "alkyl." In some embodiments, "haloalkyl" can refer to an alkyl group having one or more halogen substituents, and can be within the meaning of "alkyl." At various embodiments, a haloalkyl group can have 1 to 20 carbon atoms, for example, 1 to 10 carbon atoms (i.e., $C_1$-$C_{10}$ haloalkyl group). Examples of haloalkyl groups include $CF_3$, $C_2F_5$, $CHF_2$, $CH_2F$, $CCl_3$, $CHCl_2$, $CH_2Cl$, $C_2Cl_5$, and the like. Perhaloalkyl groups, i.e., alkyl groups where all of the hydrogen atoms are replaced with halogen atoms (e.g., perfluoroalkyl groups such as $CF_3$ and $C_2F_5$), are included within the definition of "haloalkyl." In some embodiments, "alkoxy" can refer to —O-alkyl group, and can be within the meaning of "alkyl.". Examples of alkoxy groups include, but are not limited to, methoxy, ethoxy, propoxy (e.g., n-propoxy and isopropoxy), t-butoxy groups, and the like. The alkyl group in the —O-alkyl group can be substituted with 1-5 $R^1$ groups and $R^1$ is as defined herein.

As used herein, "hydroxy protective group" refers to the generally understood definition of an alcohol or hydroxy protecting group as defined in T. W. Greene, *Protective Groups in Organic Synthesis*, John Wiley and Sons, 1991 (hereinafter "Greene, *Protective Groups in Organic Synthesis*").

As used herein, "protecting group" is used as known in the art and as demonstrated in Greene, *Protective Groups in Organic Synthesis*.

As used herein, substantially pure compound or isomer refers to one isomer being 90% of the resulting isomeric mixture, or preferably 95% of the resulting isomeric mixture, or more preferably 98% of the resulting isomeric mixture, or even more preferably 99% of the resulting isomeric mixture, and most preferably above 99% of the resulting isomeric mixture.

One aspect of the invention is a synthetic method for synthesizing Beraprost (314d) or a related analogue, such as a salt, solvate or prodrug thereof from a Corey Lactone, such as a compound represented by Formula (II)

In one embodiment, the present invention relates to a method for making a substantially pure isomer of beraprost or its related derivatives of the following formula (I):

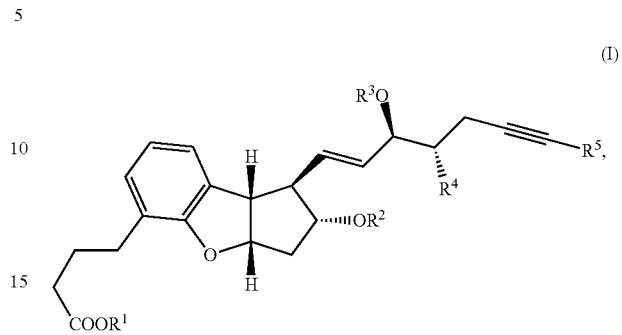

(I)

wherein $R^1$ represents a cation, H, or $C_{1-12}$ alkyl, $R^2$ and $R^3$ each represent H or a hydroxy protective group, $R^4$ represents H or $C_{1-3}$ alkyl, and $R^5$ represents H or $C_{1-6}$ alkyl, comprising:

(1) performing a cycloaddition reaction between a compound of the following formula:

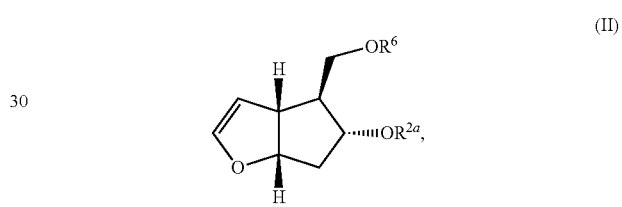

(II)

wherein in $R^{2a}$ and $R^6$ independently represent hydroxy protecting groups or H, and a compound of the following formula:

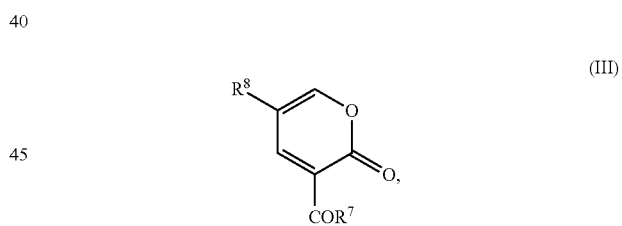

(III)

wherein $R^7$ represents $C_{1-6}$ alkoxy or $C_{1-12}$ alkyl-$COOR^9$, where $R^9$ represents $C_{1-3}$ alkyl, and $R^8$ represents halide or H to form a compound of the following formula:

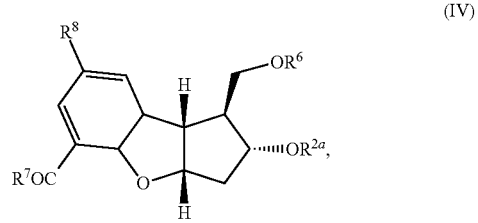

(IV)

wherein $R^{2a}$, $R^6$, $R^7$, and $R^8$ are each defined above;

(2) aromatizing the cyclodiene compound of formula (IV) to form the aromatic product of the following formula:

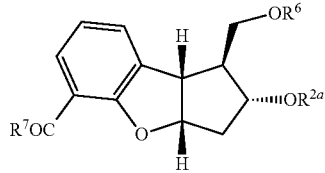
(V)

(3) reducing the ester of the compound of formula (V) to a benzyl alcohol and oxidation of benzyl alcohol to an aldehyde followed by addition of a carbon to said aldehyde to form an alkyne resulting in a compound of the following formula:

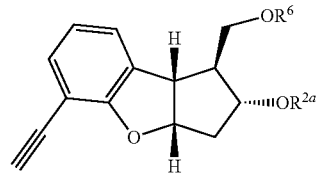
(VI)

(4) coupling the terminal alkyne with $N_2CH_2CO_2R^{1a}$, wherein $R^{1a}$ represents a $C_{1-12}$ alkyl followed by hydrogenation of the alkyne to its corresponding alkane to form a compound of the following formula:

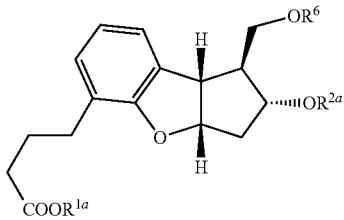
(VII)

(5) selectively deprotecting the primary hydroxyl protective group, followed by oxidation of the primary hydroxyl group to the corresponding aldehyde, followed by coupling with a side-chain of the formula:

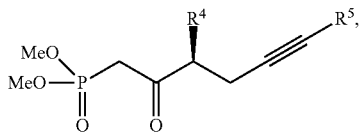
(VIII)

wherein $R^4$ and $R^5$ are each defined above and (VIII) is substantially a single isomer to form a compound of the following formula:

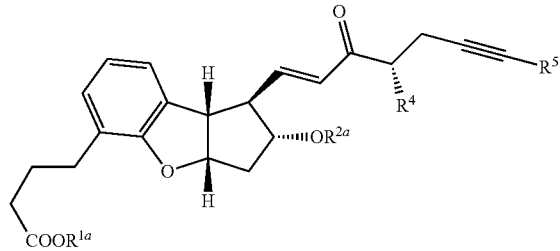
(IX)

(6) reduction of the ketone, deprotection of any remaining hydroxy protective group and optionally converting the $R^{1a}$ into a cation or H to form a compound of the following formula:

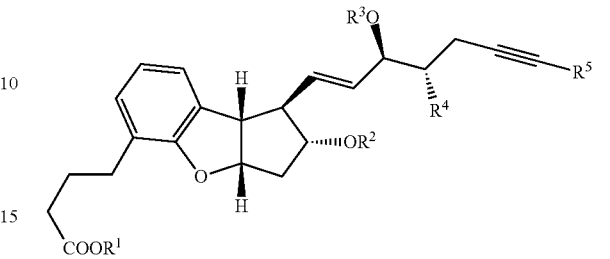
(I)

In the present invention, the single pharmacologically active isomer of beraprost corresponds to the 314-d isomer of beraprost or its corresponding salt or other pharmaceutically useful related derivative, such as for example, prodrug or solvate. This 314-d isomer compound is represented by the compound of formula (I) wherein $R^1$ is a cation or H, $R^2$ and $R^3$ are H, $R^4$ and $R^5$ are $CH_3$.

In one embodiment, $R^{2a}$ and $R^6$ independently represent hydroxy protecting groups and are different protecting groups. In one embodiment, $R^{2a}$ is a silyl protecting group, such as for example, trimethylsilyl, triethylsilyl, t-butyldimethylsilyl, t-butyldiphenylsilyl, phenyldimethylsilyl. Additional silyl protecting groups are recited in Greene, *Protective Groups in Organic Synthesis*, and are incorporated by reference. In one embodiment, $R^6$ is a protecting group that is capable of protecting a primary alcohol without reacting with a secondary alcohol, such as for example a trityl group. Additional $R^6$ protecting groups meeting this requirement may be found in Greene, *Protective Groups in Organic Synthesis*, and are incorporated by reference.

In one embodiment, the cycloaddition of step (1) may be achieved with an inverse electron demand Diels Alder reaction followed by thermal decarboxylation to form endo and exo isomers. The subsequent aromatization to compound (V) eliminates said isomers. In one embodiment, aromatization may be achieved by dehydrogenation, for example, palladium on carbon may be utilized to convert the diene of compound (IV) into the aromatic moiety of compound (V).

The reduction of the ketone in step (6) may be achieved using a non-selective reducing agent, such as for example, sodium borohydride with cerium trichloride heptahydrate, and the subsequent diastereomers separated, or alternatively a chiral reducing agent capable of selectively reducing the ketone may be used to obtain substantially one isomer of the resulting alcohol. Selective reducing agents are known in the art and include, for example: (R)-(+)-2-Butyl-CBS-oxazaborolidine and catecholborane, (R)-(+)-2-Methyl-CBS-oxazaborolidine and catecholborane, (+) DIP-chloride, $NaBH_4$ and 2-(3-Nitrophenyl)-1,3,2-dioxaborolane-4S,5S-dicarboxylic acid (D-TarB-$NO_2$), modified DIBAL reagents, and modified LAH agents.

In one embodiment, the compound of formula (I) is produced as the single isomer represented by formula (I) and in substantially isomerically pure form. In one embodiment, the product represented by formula (I) comprises 90% of the resulting isomeric mixture, or preferably 95% of the resulting isomeric mixture, or more preferably 98% of the resulting isomeric mixture, or even more preferably 99% of the resulting isomeric mixture, and most preferably above 99% of the resulting isomeric mixture.

In another embodiment of this invention is a method comprising steps (1) through (4) followed by deprotection of any alcohol protection groups to yield compound of formula (VII) wherein $R^{2a}$ and $R^6$ are H and $R^{1a}$ is methoxy. This compound is isolated as substantially one isomer represented by the compound of formula (VII).

Another aspect of the present invention provides a novel method that can attach the alpha side-chain to single-isomer key intermediate leading to the pharmaceutical compound represented by the general formula (I). The novel process provides for producing the four-carbon alpha side-chain of beraprost or its related derivatives from the core intermediate ester of the compound of formula (V) comprising conversion of the compound of formula (V) to a benzyl alcohol of formula (X) followed by oxidation of benzyl alcohol to an aldehyde of formula (XII) followed by addition of a carbon to said aldehyde to form an alkyne compound of formula (VI). One skilled in the art would appreciate that extension of the alpha side-chain may proceed from the benzyl alcohol of formula (X) by conversion of the alcohol to a leaving group such as $R^{10}$ of the formula (XI) followed by nucleophilic displacement. Furthermore, a Wittig or similar type reaction may be used to couple a side chain to the benzyl aldehyde of formula (XII).

In another embodiment, analogues of the single-isomer key intermediate may include an alpha side-chain of more than four carbons. For example Scheme 1 demonstrates that the benzyl alcohol of formula (X) can be converted to the compound of formula (XI) followed by nucleophilic displacement resulting in (XIII). In another embodiment, the aldehyde of formula (XII) may be subjected to a Wittig-type reaction to produce a compound of formula (XIII). In a further embodiment, the aldehyde of formula (VI) may be converted to a compound of formula (XIII) by methods known in the art or analogous to methods disclosed herein.

wherein in $R^{2a}$ and $R^6$ independently represent hydroxy protecting groups and $R^{10}$ to $R^{12}$ are defined above, and may be optionally substituted with one or more functional groups. A compound of formula (XIII) can be subjected to steps (5) and (6) to produce additional beraprost analogues.

Another aspect of this invention relates the side-chain coupling and variations on said side-chain, the trans-alkene of beraprost and its derivatives is achieved through Wadworth-Emmons-type reaction. The side-chain is produced as substantially a single isomer. Synthesis of the side-chain coupling product of the formula (VIII) may be achieved from a single isomer Weinreb amide compound of the following formula:

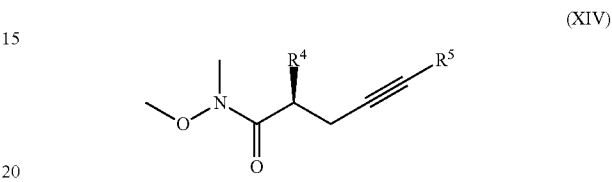

(XIV)

wherein $R^4$ and $R^5$ are each defined above.

Furthermore, the compound of formula (XIV) may be synthesized according to reagents known in the art from a compound of the formula (XV) by deprotonation and subsequent selective addition to an compound with a suitable leaving group, such as for example compound (XVI).

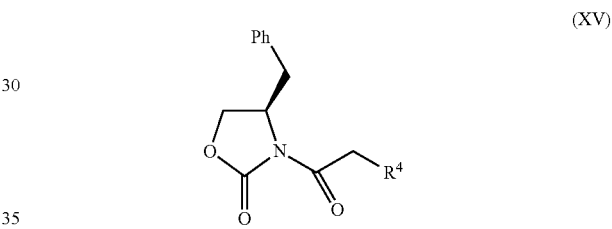

(XV)

Scheme 1

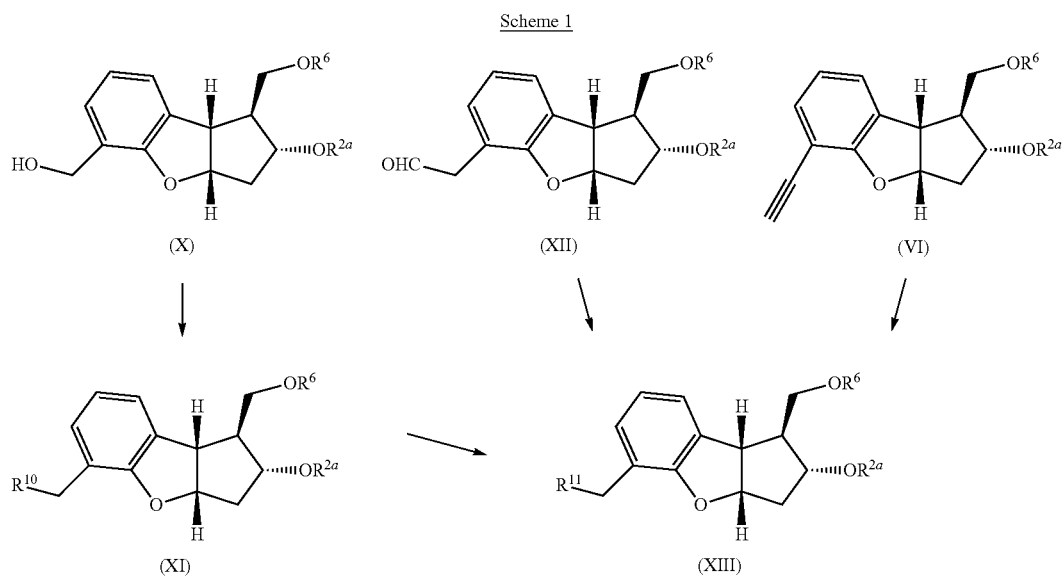

$R^{10}$ = halide, OTf, OMs, OTs
$R^{11}$ = $C_{1-12}$ alkyl-COOR$^{12}$
$R^{12}$ = H, cation, $C_{1-3}$ alkyl

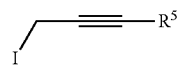

(XVI)

resulting in the compound:

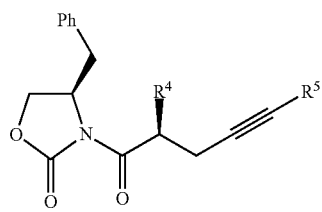

(XVII)

The compound of formula (XVII) may be converted to a compound of formula (XIV) by methods known in the art. Compound (XIV) may subsequently be converted in to a compound of the formula (VIII) by methods analogous to those disclosed herein.

Furthermore, another embodiment of this invention includes manipulation of the side chain coupling product as shown in Scheme 2. Variation of the side-chain allows additional analogues of beraprost to be explored. In one embodiment, the compound of the formula (XV) may be reacted with a compound of the formula (XVIII), wherein $R^{13}$ is $C_{1-12}$ allyl, $C_{1-12}$ alkene, $C_{1-12}$ alkyne, $C_{1-12}$ cyclo alkyl, $C_{1-12}$ cyclo alkene, or $C_{1-12}$ cyclo alkyne, and further manipulated by methods analogous to those disclosed herein or known in the art to form a Weinreb amide of formula (XIX). The methods for these reactions are analogous to those for the production of compound (XIV) or are known in the art. A compound of the formula (XIX) may then be converted into a coupling product suitable for Wadworth-Emmons-type coupling analogous to compound of formula (VIII). The resulting coupling product may be coupled with a compound suitable for Wadworth-Emmons-type coupling disclosed herein, for example a compound of the formula (VII) that has been selectively deprotected at the primary hydroxyl protective group, followed by oxidation of the primary hydroxyl group to the corresponding aldehyde.

Scheme 2

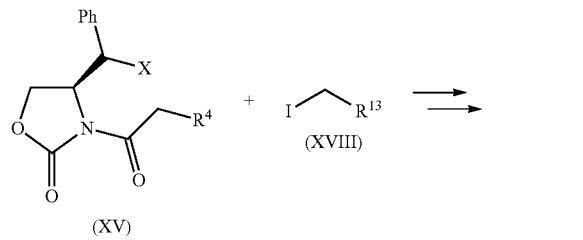

wherein $R^4$ and $R^{13}$ are previously defined. In one embodiment, X is H. In another embodiment, X is Ph. Additional moieties, such as analogues of Ph and other aryl, heteroaryl or alkyl moieties may also serve as X. In one embodiment, the phosphonate product is produced with chiral purity of 97 percent or more, or 99 percent or more.

Additional embodiments include side-chain compounds represented by the structures

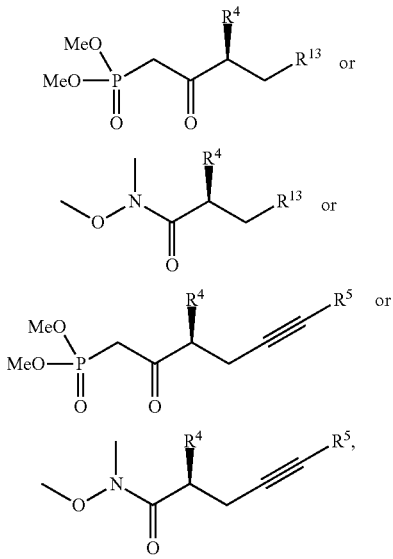

wherein $R^4$, $R^5$ and $R^{13}$ are previously defined and the chiral purity is 97 percent or more, or 99 percent or more. A preferred embodiment includes compounds represented by the structures

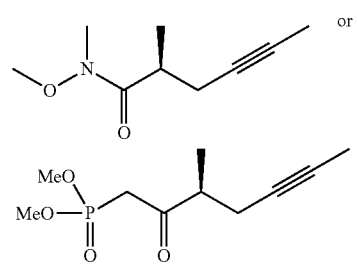

wherein the chiral purity is 97 percent or more, or 99 percent or more.

Side-chain compounds may be produced by the methods described herein, including the exemplary methods shown in FIG. 1

The present invention is further illustrated by, though in no way limited to, the following examples.

Example 1

Synthetic Route to the Single Isomer of a Compound of Formula (I)

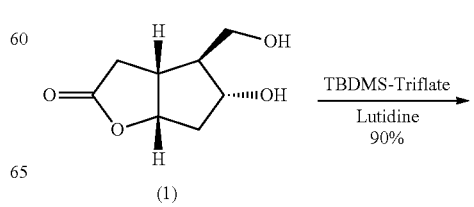

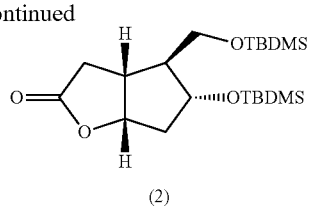

(2)

Preparation of (2)

A 1-L, three-necked, round-bottomed flask equipped with a mechanical stirrer, a dropping funnel, a thermocouple and an argon inlet-outlet adapter connected to a bubbler was charged with Corey lactone (1) (10 g), anhydrous dichloromethane (100 mL), and 2,6-lutidine (27 mL) under argon. A solution of t-butyldimethyl trifluoromethane sulfonate (37.4 mL) in dichloromethane (50 mL) was added to the reaction mixture drop-wise, while keeping the temperature between −10° C. to −20° C. over a period of 20-40 minutes. After complete addition, the reaction mixture was allowed to warm-up to ambient temperature. After 2-4 h, the progress of the reaction was monitored by thin-layer chromatography. After completion of the reaction, the reaction mixture was concentrated in vacuo to obtain a crude product. The crude product was chased with MTBE to remove dichloromethane completely. The crude product was dissolved in MTBE (100-150 mL) and washed with water (1×100 mL), saturated sodium bicarbonate (1×100 mL), brine (1×150 mL), dried over anhydrous sodium sulfate (10 g), and filtered. The filtrate was evaporated in vacuo to a afford crude, viscous liquid (30.4 g). The crude product was purified by column chromatography using 230-400 mesh silica gel. A solvent gradient of ethyl acetate in hexanes (2-12%) was used to elute the product from the column. All fractions containing the desired product were combined and concentrated in vacuo to give pure product (2) as a white solid (20.8 g, 89.4%).

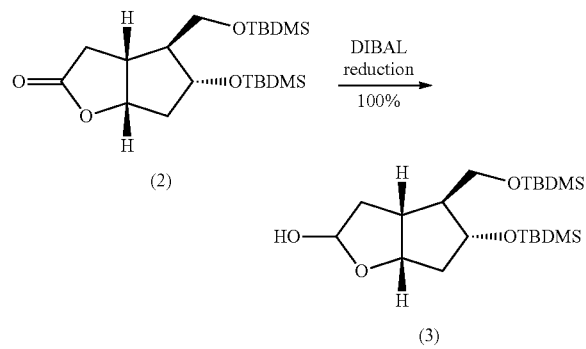

Preparation of (3)

A 1-L, two-necked, round-bottomed flask equipped with a mechanical stirrer, a dropping funnel, a thermocouple and an argon inlet-outlet adapter connected to a bubbler was charged with intermediate 2 (20.0 g), and toluene (200 mL). The temperature of the reaction mixture was maintained at −50° C. to −70° C. under nitrogen using dry-ice-acetone bath. While maintaining the temperature of the reaction mixture at −50° C. to −70° C., diisobutylaluminium hydride (DIBAL, 60 mL, 1.0M in toluene) was added drop wise during 20-30 minutes. The progress of the reaction was monitored by TLC. The reaction mixture was quenched with methanol (10 mL) at −20° C., water (300 mL), followed by addition of diluted hydrochloric acid (~20%). The organic layer was separated and aqueous layer was extracted with MTBE (2×100 mL). The combined organic layers were washed with saturated sodium bicarbonate (1×150 mL), brine (1×150 mL) and, dried over sodium sulfate (10 g). The organic layer was filtered. The filtrate was concentrated in vacuo, to give a yellow, viscous oil (20.4 g). The crude product was used as such in the next step.

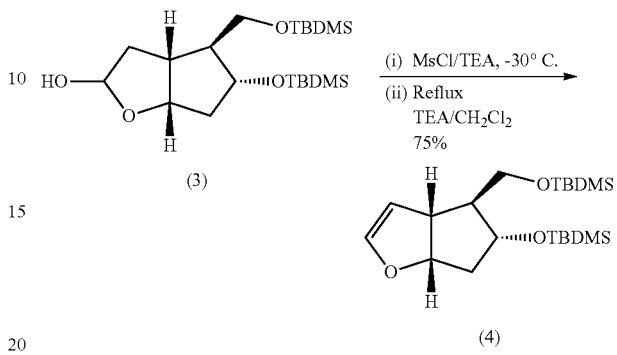

Preparation of (4)

A 1-L, three-necked, round-bottomed flask equipped with a mechanical stirrer, a thermocouple, and an argon inlet-outlet trap was charged with lactol intermediate 3 (20 g), anhydrous dichloromethane (200-250 mL), triethylamine (69.2 mL), and dimethylamino pyridine (DMAP, 0.6 g). The temperature of the reaction mixture was reduced to −20° C. A solution of methanesulfonyl chloride (7.7 mL) was added drop wise under argon while keeping the temperature around −20° C. After complete addition, the progress of the reaction was monitored by TLC. The temperature of the reaction mixture was allowed to warm-up to ambient temperature. The reaction mixture was heated to reflux for 2-4 h. The reaction mixture was concentrated in vacuo to obtain crude product. The crude product was purified by column chromatography using 230-400 mesh silica gel and eluted with a gradient solvent of ethyl acetate in hexanes (0-10%). The fractions containing the desired product were combined and evaporated in vacuo to afford intermediate 4 (as a viscous liquid, 11 g).

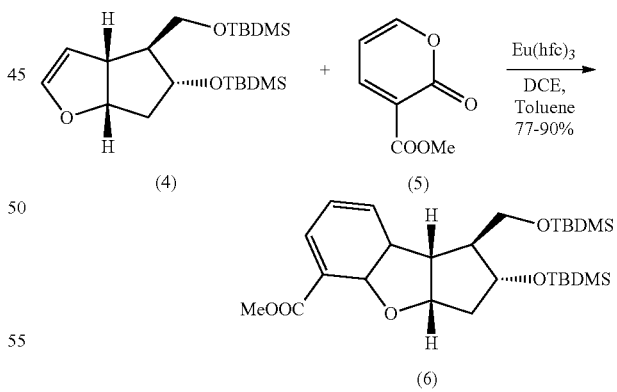

Preparation of (6)

A 1-L, two-necked, round-bottomed flask equipped with a mechanical stirrer, and an argon inlet-outlet trap was charged with a solution of intermediate (4, 10.0 g), dichloroethane (DCE, 100-150 mL), compound 5 (2.6 g), and Eu(hfc)$_3$ (1.4 g) at room temperature under argon. The reaction mixture was stirred and heated to reflux for 1.0 h and the progress of the reaction was monitored by TLC in order to ensure that starting material 5 has been consumed completely. After 1.0 h, the temperature of the reaction was reduced below reflux temperature and compound 5 (1.0 g) was added to the reaction mixture. The temperature of the reaction was increased to reflux. In a similar manner, after half an hour, compound 5 (0.9 g) was added and the reaction was continuously refluxed again. When the TLC of the reaction mixture indicated almost complete consumption of intermediate 4, the solvent was evaporated under vacuum to give a residual viscous liquid. The brown, viscous liquid was chased with toluene and dissolved in toluene (100-150 mL). The reaction mixture was heated to reflux again for 6-8 h. The progress of the reaction was monitored by TLC. After completion of the reaction, it was concentrated in vacuo to obtain the crude product 6 as a viscous oil. The crude product was purified by column chromatography using 230-400 mesh silica gel and eluted with a gradient solvent of ethyl acetate in hexanes (4-40%). The fractions containing the desired product were combined and concentrated in-vacuo to yield the intermediate 6, as a colorless, viscous oil (9.87 g, 77%).

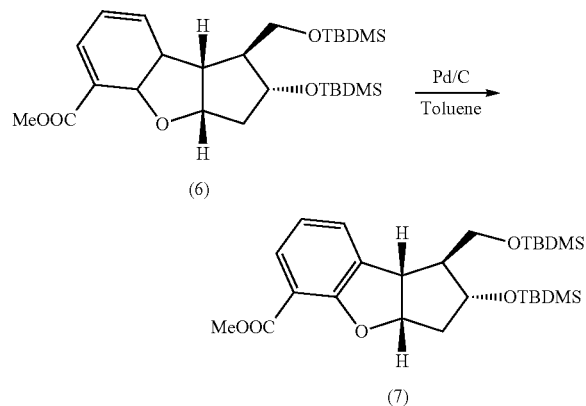

Preparation of (7)

A 500-mL, one-necked, round-bottomed flask equipped with a magnetic stirrer, an argon inlet-outlet trap, and a condenser was charged with a solution of intermediate 6 (7.6 g) in toluene (70-100 mL) under argon. At room temperature, palladium on carbon (1.52 g, 5%, 50% wet) was charged, and the reaction mixture was heated to reflux for 8-12 h. The reaction mixture was allowed to cool to room temperature, and the reaction mixture was filtered through a pad of Celite. The filtrate was concentrated in-vacuo to yield crude product 7, as a viscous liquid. The crude product 7 was purified by column chromatography using 230-400 mesh silica gel. A solvent gradient of ethyl acetate in hexanes (0-15%) was used to elute the product from the column. The fractions containing the desired product were evaporated in-vacuo to yield pure key intermediate (7) as viscous liquid (4.0 g, 43%).

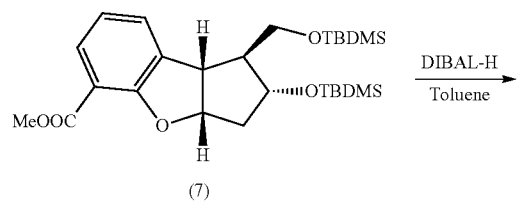

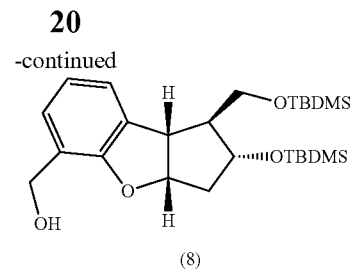

Preparation of (8)

A 500-mL, three-necked, round-bottomed flask equipped with a magnetic stirrer, and an argon inlet-outlet trap, and a thermocouple was charged with a solution of intermediate 7 (3.90 g) in toluene (40-60 mL, anhydrous). The reaction mixture was cooled to −25° C. to −50° C., and diisobutylaluminium hydride solution (DIBAL, 16.60 mL, 1.0M in toluene) was added drop-wise, while keeping the temperature of the reaction mixture between −25° C. to −50° C. The reaction mixture was stirred for 1-2 h. The progress of the reaction was monitored by TLC. The reaction mixture was quenched with methanol (2-4 mL), followed by acidification with dilute hydrochloric acid (20%, 50 mL). The organic layer was separated and aqueous layer was extracted with MTBE (2×50 mL). The combined organic layers were washed with saturated sodium bicarbonate (1×50 mL), brine (1×50 mL), and dried over sodium sulfate (10 g). The organic layer was filtered. The filtrate was concentrated in vacuo, to give a viscous oil (8, 3.73 g).

The crude product 8 was used as such in next step.

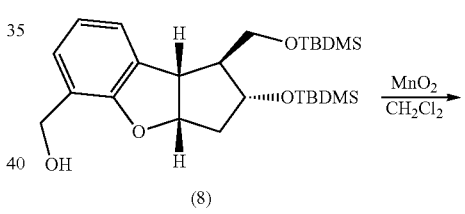

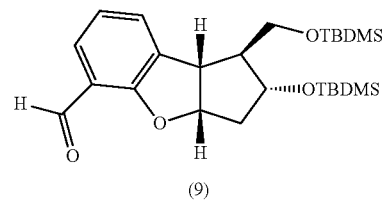

Preparation of (9)

A 500-mL, one-necked, round-bottomed flask equipped with a magnetic stirrer was charged with a solution of intermediate 8 in dichloromethane (40-70 mL), and manganese dioxide (8.30 g) under nitrogen. The reaction mixture was stirred vigorously at ambient temperature over night. The progress of the reaction was monitored by TLC. The reaction mixture was filtered through a pad of Celite and the filtrate was concentrated in-vacuo to obtain the crude product 9 as colorless, viscous liquid oil (3.4 g, 92%). In this case the crude product was used as such in the next step (as the TLC indicated pure material). The crude product 9 may optionally be purified by column chromatography.

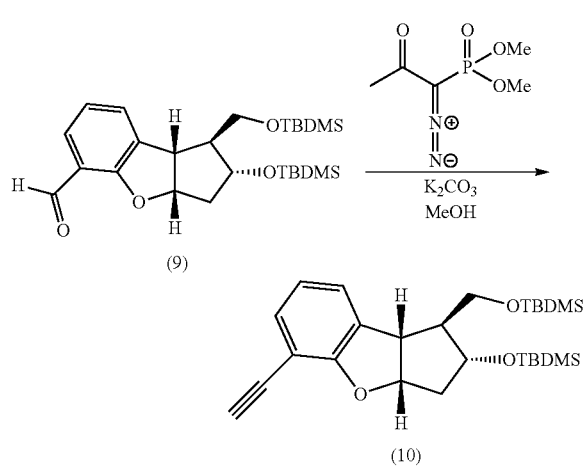

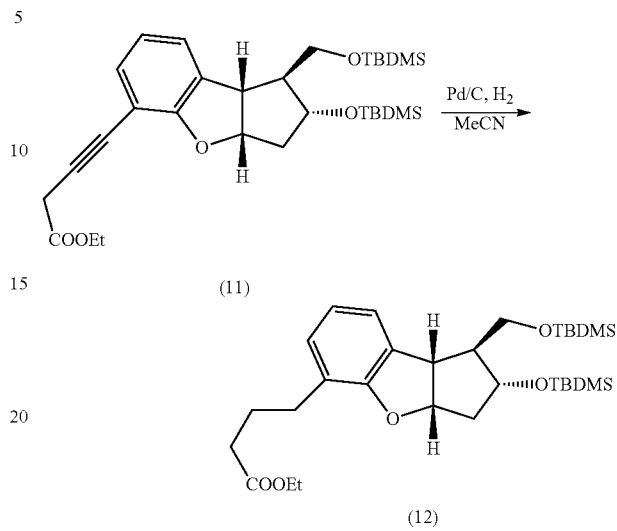

Preparation of (10)

A 50-mL, one-necked, round-bottomed flask equipped with a magnetic stirrer, and an argon inlet-outlet trap was charged with a solution of intermediate 9 (260 mg) in methanol (5-10 mL), potassium carbonate (232 mg), and dimethyl (1-diazo-2-oxopropyl)phosphonate (215 mg) at room temperature under argon. The mixture was stirred at ambient temperature over night. After ~16 h, the progress of the reaction was monitored by TLC. The solvent was evaporated in vacuo and dissolved in MTBE (10-15 mL). The organic layer was washed with brine (1×10 mL), dried over anhydrous sodium sulfate, filtered, and the filtrate concentrated in vacuo to obtain crude product 10, as a viscous oil.

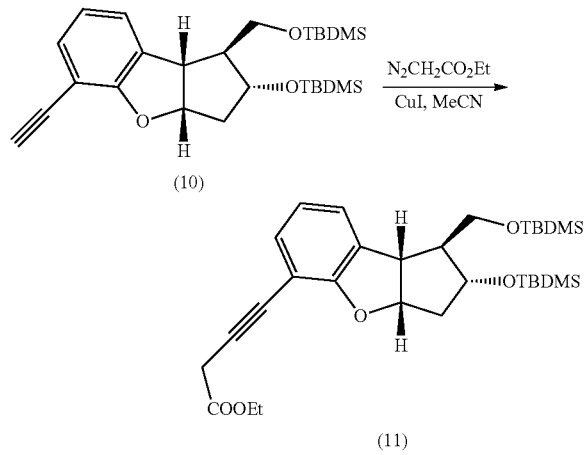

Preparation of (11)

A 50-mL, one-necked, round-bottomed flask equipped with a magnetic stirrer, and an argon inlet-outlet trap was charged with a solution of intermediate 10 (55 mg) in acetonitrile (5-10 mL), and copper iodide (3 mg) at room temperature under nitrogen. To the stirred solution, ethyl diazoacetate (14 mg dissolved in 1.0 mL of acetonitrile) was added. The reaction mixture was stirred overnight. The progress of the reaction was monitored by TLC. The reaction mixture was concentrated in-vacuo to give the crude product 11. The crude product was purified by column chromatography using 230-400 mesh silica gel and the column was eluted with a gradient solvent of ethyl acetate in hexanes (0-10%). The fractions containing the desired compound were evaporated in vacuo to yield intermediate 11, as a colorless, viscous oil (38 mg, 60%).

Preparation of (12)

A 50-mL, three-necked, round-bottomed flask equipped with magnetic stirrer was charged with a solution of intermediate 11 (50 mg) in anhydrous acetonitrile (5-10 mL) and palladium on carbon (10 mg, 5%, wet 50%). The reaction mixture was stirred and air was removed by vacuum. The vacuum in the flask was replaced by hydrogen from an attached balloon. The process was repeated 5-10 times. Finally, the reaction mixture was stirred at room temperature under hydrogen overnight. The progress of the reaction was monitored by TLC. After completion of the reaction, the reaction mixture was filtered through a pad of Celite and the filtrate concentrated in-vacuo to give the crude product 12. The crude product 12 was purified by flash column chromatography using 230-400 mesh silica gel. A solvent gradient of ethyl acetate in hexanes (2-8%) was used to elute the product from the column. The fractions containing the desired product 12 were combined and evaporated in-vacuo to yield product 12, 41 mg (~80%).

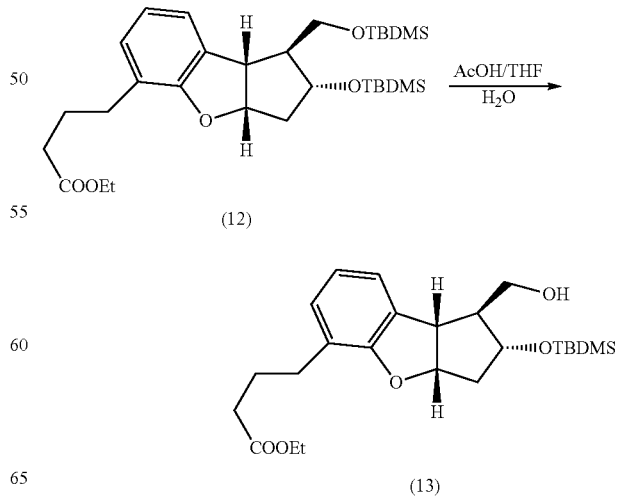

Preparation of (13)

A 25-mL, one-neck, round-bottomed flask equipped with a magnetic stirrer was charged with intermediate 12 in a solution of acetic acid:THF:water (1.0:3.0:0.5). The reaction mixture was stirred at ambient temperature overnight. The progress of the reaction was monitored by TLC. After approximately 90% completion of the reaction (by TLC), the reaction mixture was concentrated in-vacuo to give a residual viscous liquid. The crude product was dissolved in ethyl acetate (10 mL) and organic layer was washed with saturated sodium bicarbonate solution (1×10 mL), brine (1×10 mL), dried over anhydrous sodium sulfate (1.0 g), filtered and the filtrate evaporated in-vacuo. The crude product 13 was purified by column chromatography using 230-400 mesh silica gel. A solvent gradient of ethyl acetate in hexanes (4-100%) was used to elute the products from the column. The fractions containing the desired product 13 were combined and evaporated in-vacuo to yield a viscous liquid of pure product 13, (120 mg). The purification of crude product by column also gave starting material 12 (36 mg), diol product (52 mg).

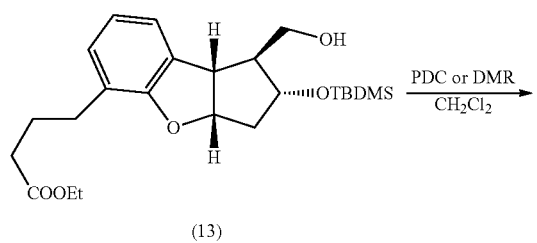

(13)

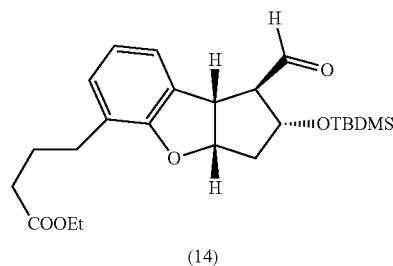

(14)

Preparation of (14)

A 100-mL, one-neck, round-bottomed flask equipped with a magnetic stirrer, an argon inlet-outlet trap was charged with a solution of intermediate 13 (160 mg) in dichloromethane (5-10 mL). To the stirred solution, add Dess-Martin reagent (233 mg) at ambient temperature under nitrogen. The reaction mixture was stirred for 0.5-1.0 h. The progress of the reaction was monitored by TLC. The reaction mixture was quenched with NaHCO$_3$ (solid powder, 500 mg). The product 14 was purified by column chromatography using 230-400 mesh silica gel by loading the reaction mixture directly on the column, and the column was eluted with dichloromethane (100%). The fractions containing the desired product 14 were evaporated in-vacuo to yield pure product 14 (125 mg, 73%).

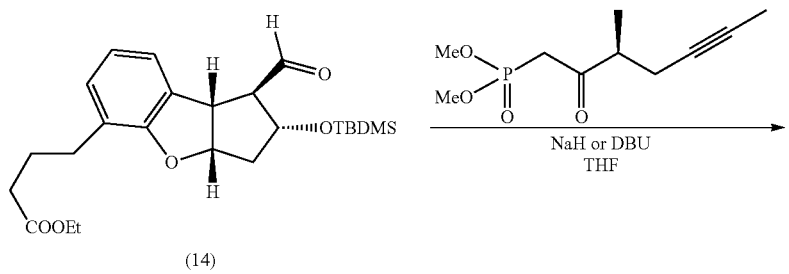

(14)

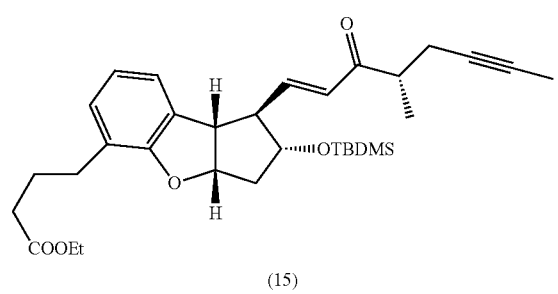

(15)

Preparation of (15)

A 50-mL, three-neck, round-bottomed flask equipped with a magnetic stirrer and an argon inlet-outlet trap was charged with the phosphonate side-chain (57 mg), THF (5 mL), and sodium hydride (9.0 mg). The mixture was stirred at 0-10° C. for 15-20 minutes under nitrogen. The intermediate 14 (85 mg, dissolved in 5 mL of THF) was added drop-wise during a period of 5-10 minutes. The reaction mixture was stirred 2-3 h. The temperature of the reaction mixture was allowed to rise to ambient temperature. The progress of the reaction was monitored by TLC after 2-3 h. The reaction mixture was quenched with acetic acid (couple of drops) and the reaction mixture was extracted with MTBE (3×10 mL). The combined organic layers were washed with saturated sodium bicarbonate (1×10 mL), brine (1×10 mL), dried over anhydrous sodium sulfate, filtered, and evaporated in-vacuo to give a crude product. The crude product 15 was purified by column chromatography using 230-400 mesh silica gel, the column was eluted with gradient of ethyl acetate and hexanes (5-12%). The pure fractions containing the desired compound 15 were combined and evaporated in-vacuo to yield pure product 15 as a viscous liquid (72 mg, 70%).

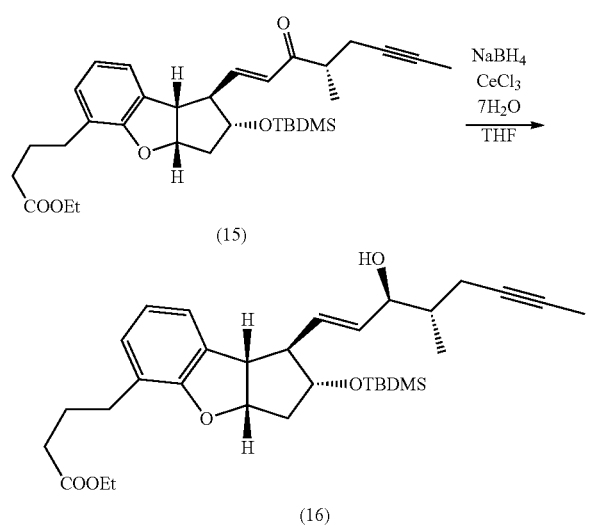

Preparation of (16)

A 50-mL, one-neck, round-bottomed flask equipped with a magnetic stirrer, was charged with a solution of intermediate 15 in methanol and cerium chloride heptahydrate (CeCl$_3$.7H$_2$O, 28 mg). To the reaction mixture, sodium borohydride (1.74 mg) was added and the reaction mixture was stirred at temperature 0-10° C. for 1-2 h. The progress of the reaction was monitored by TLC. The reaction mixture was quenched with acetic acid (0.2 mL), saturated solution of ammonium chloride (2 mL) and brine (10 mL). The reaction mixture was extracted with ethyl acetate (3×15 mL). The combined organic layers were washed with brine, dried over anhydrous sodium sulfate, filtered, and evaporated in-vacuo to give crude product 16 (46 mg). The crude product was used as such in the next step.

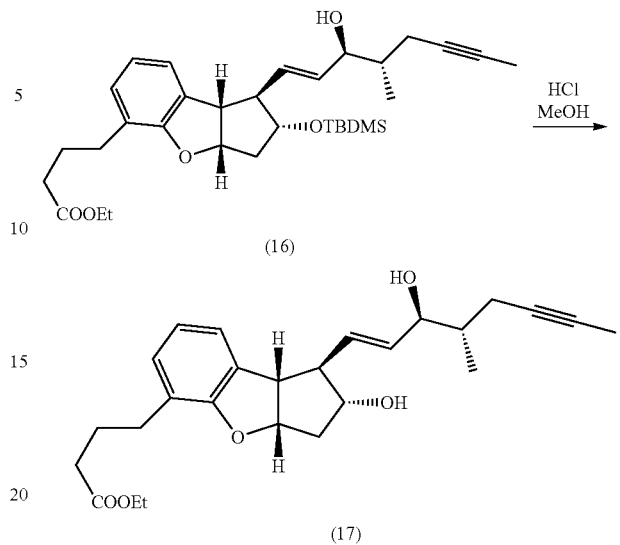

Preparation of (17)

A 50-mL, one-neck, round-bottomed flask equipped with a magnetic stirrer, was charged with a solution of intermediate 16 in methanol and hydrochloric acid (a few drops). The reaction mixture was stirred at ambient temperature for 1-2 h. The progress of the reaction was monitored by TLC. The reaction mixture was quenched with a solution of saturated sodium bicarbonate, then brine (10 mL) and extracted with ethyl acetate (3×10 mL). The combined organic layers were washed with brine (1×10 mL), and dried over anhydrous sodium sulfate (1 g), filtered, and the filtrate was evaporated in-vacuo to give crude product. The crude product was purified by column chromatography using 230-400 mesh silica gel and eluted with ethyl acetate in hexanes (10-70%). The fractions containing the desired product (lower spot on TLC) were evaporated in-vacuo to yield pure product 17 (22 mg, ~50% over two steps, one isomer only).

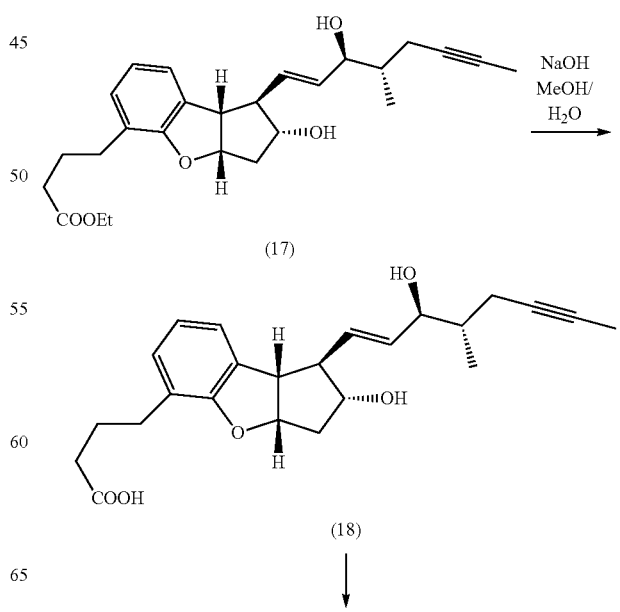

-continued

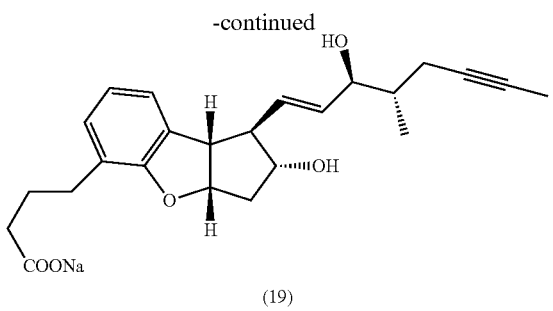

(19)

-continued

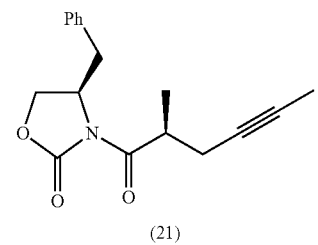

(21)

Preparation of (18)

A 50-mL, one-neck, round-bottomed flask equipped with a magnetic stirrer, was charged with a solution of intermediate 17 in methanol and the solution of sodium hydroxide (15 mg in 1.0 mL of water). The reaction mixture was stirred at ambient temperature overnight. The progress of the reaction was monitored by TLC. Additional amount of sodium hydroxide (25 mg dissolved in 1.0 mL of water) was added and temperature of the reaction mixture was raised to 45° C.-55° C. for 6-8 h. The progress of the reaction was monitored by TLC. The solvent was evaporated in-vacuo to remove methanol, and water was added to the reaction mixture. The aqueous layer was extracted with dichloromethane (3×10 mL) to remove impurities. The pH of the aqueous layer was adjusted to 2-3 by addition of dilute hydrochloric acid and the aqueous layer was extracted with ethyl acetate (3×10 mL). The combined organic layers were washed with water (1×10 mL), brine (1×10 mL), and dried over anhydrous sodium sulfate (1 g), filtered, and the filtrate was evaporated in-vacuo to give crude product (314-d isomer of beraprost, 18 mg).

Preparation of (19)

A 50-mL, one-neck, round-bottomed flask equipped with a magnetic stirrer, was charged with a solution of free 314-d isomer of beraprost (18) in methanol and the solution of sodium hydroxide (2 mg dissolved in 1.0 mL of water). The reaction mixture was stirred at ambient temperature for 1-2 h. The solvent was evaporated in-vacuo to remove methanol and water. Toluene (5 mL) was added to the residual, yellow, and viscous material and the toluene was removed in-vacuo to give the solid sodium salt 314-d isomer of beraprost (21 mg). A chiral HPLC assay indicated 314-d isomer of beraprost (84%) and it was confirmed by comparing with references of 314-d isomer of beraprost (one reference consists of 314-d isomer of beraprost and other reference consists of mixture of four isomers including 314-d isomer of beraprost).

Example 2

Side-Chain Formation

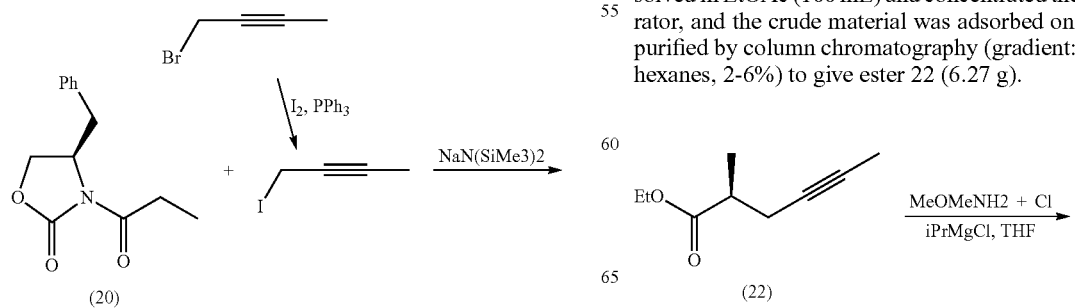

Preparation of (21)

The benzyl-substituted oxazolidinone 20 was selected as the starting material. It had given a high selectivity in the synthesis. Deprotonation of 20 with NaN(SiMe$_3$)$_2$ and treatment of the corresponding sodium enolate with freshly prepared 1-iodo-2-butyne, which was prepared from the commercially available 1-bromo-2-butyne, gave the substituted oxazolidinone 21 in 70-90% yield. Reaction of oxazolidinone 21 with 1-bromo-2-butyne never went to completion, even with excess of reagent. 1-iodo-2-butyne can be prepared from 2-butyn-1-ol or 1-bromo-2-butyne, whereas the in-situ preparation of 1-iodo-2-butyne from 1-bromo-2-butyne is more convenient and preferable.

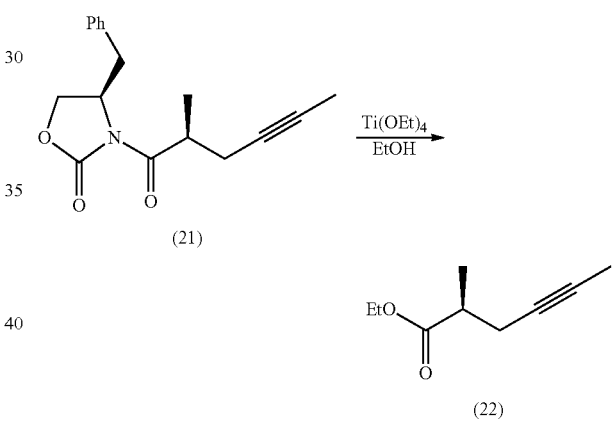

Preparation of (22)

To a 250 mL, three-necked, round-bottomed flask equipped with a mechanical stirrer and an argon inlet-outlet adapter connected to a bubbler was charged with a solution of oxazolidinone 21 (8.095 g) in EtOH (100 mL), followed by addition of Ti(OEt)4 (6.473). The mixture was heated to reflux for 7-10 h. The reaction mixture was concentrated in a rotary evaporator at 20° C./50 mbar. The residue was dissolved in EtOAc (100 mL) and concentrated the rotary evaporator, and the crude material was adsorbed on silica gel and purified by column chromatography (gradient: ethyl acetate/hexanes, 2-6%) to give ester 22 (6.27 g).

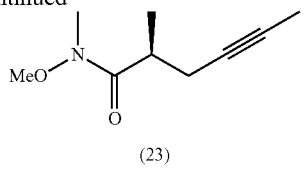

(23)

Preparation of (23)

To a 250 mL, three-necked, round-bottomed flask equipped with a mechanical stirrer and an argon inlet-outlet adapter connected to a bubbler was charged with a solution of ester 22 (6.0 g) and [MeO(Me)NH$_2$]Cl (9.5 g) in THF (75 mL). To the solution was added drop-wise i-PrMgCl (48.6 mL, 2.0 M in THF) at 20° C. during 45 min by a dropping funnel. After the mixture was stirred at 20° C. for 30 min, aqueous NH$_4$Cl (4 mL) was added. The mixture was allowed to warm to ambient temperature and diluted with MTBE (25 mL). The suspension was filtered through a pad of Celite and concentrated in vacuo. The crude product was purified by column chromatography (gradient: EtOAc/hexanes, 5-25%) to afford Weinreb amide 23 (3.45 g, 73% over two steps) as a colorless oil.

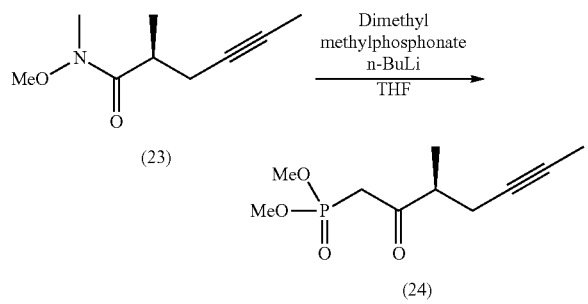

Preparation of (24)

To a 250 mL, three-necked, round-bottomed flask equipped with a mechanical stirrer and an argon inlet-outlet adapter connected to a bubbler was charged with a solution of Dimethyl methylphosphonate (5.279 g) in THF (30 mL), followed by drop-wise addition of n-BuLi (22.16 mL of 1.6 M in hexanes) at 78° C. by a dropping funnel. The mixture was stirred at 78° C. for 1 h and then a solution of amide 23 (3.00 g) in THF (20 mL) was added during 30-45 minutes via the dropping funnel. After the mixture was stirred at 78° C. for 2 h, aqueous NH$_4$Cl (4 mL) was added. The reaction mixture was allowed to warm to ambient temperature, diluted with MTBE (50 mL), filtered and concentrated in vacuo. The crude product was purification by column chromatography (gradient, EtOAc/hexanes, 0-8%) to afford phosphonate 24 (3.799 g, 92%).

Example 3

Preparation of Enone Intermediate from Ester Diol

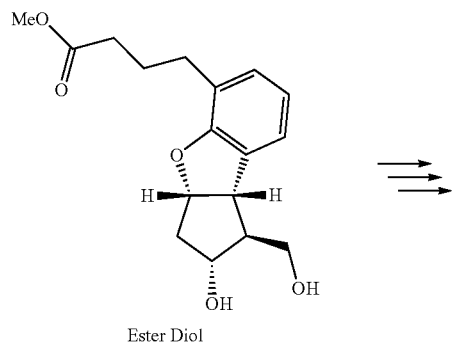

Ester Diol

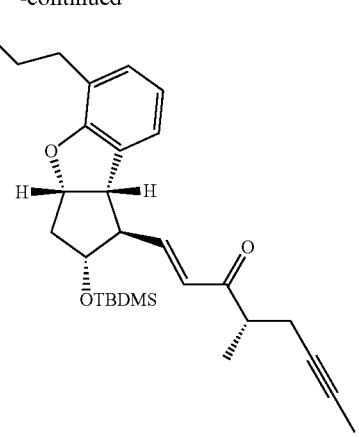

Enone Intermediate

Step 1: Protection of the Primary Alcohol

A 500 mL, two-necked, round-bottom flask equipped with a magnetic stir bar and an argon inlet-outlet adapter was charged with a solution of ester diol (1) (10.00 g) in dichloromethane (200 mL). To this solution triethylamine (13.21 g), 4-(dimethylamino)pyridine (4.0 g), and DMF (20 mL) were added at ambient temperature under argon. The mixture was stirred until a clear solution was obtained. The reaction was stirred for ~31 h at ambient temperature. After ~31 h, the progress of the reaction was monitored by TLC. The mixture was washed with saturated ammonium chloride (200 mL). The organic layer was separated, dried over anhydrous sodium sulfate, filtered, and concentrated in vacuo to give the crude product (2) as a viscous oil. The crude product from another 10-g batch was combined and purified by column chromatography using 230-400 mesh silica gel and eluted with a gradient solvent of ethyl acetate in hexanes (5-50%). The fractions containing the desired compound (by TLC) were evaporated in vacuo to yield trityl ether (2) (33.82 g, 94.6% from two 10-g batches). The compound was characterized by spectral data.

Step 2: Protection of the Secondary Alcohol

A 1000 mL, two-necked, round-bottom flask equipped with a magnetic stir bar and an argon inlet-outlet adapter was charged with a solution of trityl ether (2) (39.50 g) in anhydrous dichloromethane (600 mL). To this solution, 2,6-lutidine (18.51 g) was added at ambient temperature under argon. The mixture was stirred until a clear solution was obtained. The mixture was cooled to −15° C. and TBDMS triflate (22.84 g) was added in portions while maintaining the temperature below −10° C. The reaction was stirred for ~1 h and the progress of the reaction was monitored by TLC. At this stage the reaction was complete. To the reaction mixture hexanes were added (600 mL) and temperature was allowed to rise to ambient. This mixture was passed through a pad of 230-400 mesh silica gel (384 g) and eluted with a gradient solvent of ethyl acetate in hexanes (5-15%). The fractions containing the desired compound were evaporated in vacuo to yield silyl ether (3) (47.70 g, 99.6%). The compound was characterized by spectral data.

Step 3: Deprotection of the Primary Alcohol

A 500 mL, two-necked, round-bottom flask equipped with a magnetic stir bar and an argon inlet-outlet adapter was charged with a solution of trityloxy-TBDMS ether (3) (14.58 g) in anhydrous dichloromethane (175 mL). To this solution, diethylaluminum chloride (22.00 mL, 1M in dichloromethane, 1.0 eq.) was added at ambient temperature under argon. The reaction was stirred for ~3 h and the progress of the reaction was monitored by TLC. At this stage reaction was not complete and an extra one equivalent of diethylaluminum chloride (22.00 L, 1M in dichloromethane, 1.0 eq.) was added at ambient temperature, and the reaction mixture was stirred for another 3 h while the progress was monitored by TLC. After a total of 6 h the reaction mixture showed the presence of some starting material and another 0.5 equivalent of diethyl aluminum chloride (11.00 mL, 1M in heptane, 0.5 eq.) was added at ambient temperature and reaction mixture was stirred for another 1 h and progress of the reaction was monitored by TLC. At this stage reaction was complete, and the reaction mixture was cooled to 0° C. To the reaction mixture, saturated sodium bicarbonate solution (240 mL) was added (Note 2). Once the temperature raised to ambient, and the compound was extracted with dichloromethane. The combined extracts of dichloromethane were washed with brine, dried over sodium sulfate and evaporated in vacuo to obtain a crude, viscous oil (14.01 g). This crude compound was passed through a pad of 230-400 mesh silica gel (197 g) and eluted with a gradient solvent mixture of ethyl acetate in hexanes (10-50%). The fractions containing the desired compound were evaporated in vacuo to yield hydroxy-silyl ether (4) (8.54 g, 92.3%). The compound was characterized by spectral data.

Step 4: Oxidation of Primary Alcohol and Coupling Resulting in Enone Intermediate To a cooled (−78° C.) and stirred solution of oxalyl chloride (23.00 mL) in dichloromethane (60 mL) was added slowly a solution of dimethyl sulfoxide (4.33 mL) in dichloromethane (35 mL) under argon. After stirring for 45 minutes at −78° C. to −70° C., a solution of alcohol (4) (8.54 g) in dichloromethane (60 mL) was added to this reaction mixture while maintaining the temperature below −65° C. After stirring for 60 minutes at −65° C., temperature of reaction mixture was raised to −45° C. to −40° C. and stirred for 60 minutes at this temperature. This reaction mixture was cooled to −65° C. and quenched by slow addition of triethylamine (14.15 mL) (Note 1). The reaction mixture was stirred for another 30 minutes at −65° C. and the completion of reaction was checked by the TLC. The temperature of reaction mixture was raised to ambient and water (60 mL) was added. The two-phase mixture was stirred for 5 minutes at room temperature after which the organic phase was separated and the aqueous phase was extracted with dichloromethane (2×75 mL) to ensure complete extraction of product into the organic layer. The combined organic extracts were washed with brine (100 mL), dried over sodium sulfate and evaporated in vacuo to obtain crude aldehyde (9.77 g). In a separate 500-mL, two-necked, round-bottom flask equipped with a magnetic stir bar and an argon inlet-outlet adapter, a solution of phosphonate side chain (8.50 g) in MTBE (175 mL) was charged. To this LiOH.H20 (1.86 g) was added and the mixture was stirred for −1 h. After −1 h, a solution of crude aldehyde (5) in MTBE (175 mL) was added slowly over a period of 10 minutes and stirred until completion of reaction (Note 3). Progress of reaction was monitored by TLC (Note 3). After the reaction was complete, the reaction mixture was quenched by adding water (175 mL) and the mixture stirred for 15 minutes. The organic layer was separated and aqueous layer was extracted with ethyl acetate (3×70 mL). The combined organic extracts were washed with water (70 mL), brine (30 mL), dried over sodium sulfate and evaporated in vacuo to obtain a crude, viscous liquid of enone intermediate (6) (11.22 g). This crude enone intermediate (6) was passed through a pad of 230-400 mesh silica gel (328 g) and eluted with a gradient solvent of ethyl acetate in hexanes (2-20%). The fractions containing the desired compound were evaporated in vacuo to yield enone (6) (19.42 g, 80%; This crude compound was combined with 14.99 g of crude compound from another lot and a combined column chromatography was performed on two lots). The pure compound was characterized by spectral data.

Example 4

Preparation of Compound (A)

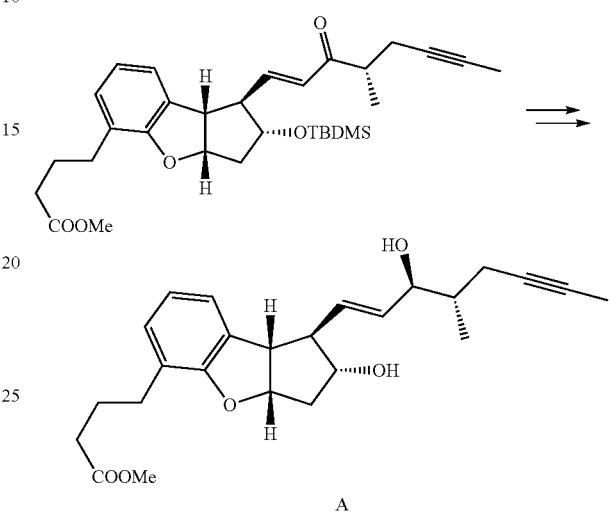

A

Option 1: Reduction/Deprotection

Step 1: Selective Reduction

A 100 mL, three-necked, round-bottom flask equipped with a magnetic stir bar, a thermocouple, and an argon inlet-outlet adapter was charged with enone compound (0.11 g) and anhydrous toluene (5.0 mL). A solution of (R)-(+)-2-methyl CBS oxazaborolidine (1.0 M in toluene) (0.43 mL) was added under argon at ambient temperature. The mixture was cooled to ~0° C. (dry ice/acetone-bath), and borane-methyl sulfide complex (0.32 mL) was added slowly maintaining the temperature between −40° C. and −30° C. After complete addition, the reaction mixture was stirred for 1-2 h at −30° C. to −25° C. The progress of the reaction was monitored by TLC. The reaction mixture was carefully quenched by slow addition of methanol (2.0 mL) over a period of 2-3 minute maintaining the temperature between −15° C. and −10° C. The reaction mixture was allowed to warm to room temperature and the stirring was continued for another 20-30 minutes. At this stage, saturated aqueous ammonium chloride solution (5.0 ml) was added with stirring. The organic layer was separated, and the aqueous layer was extracted with ethyl acetate (2×15 mL). The combined organic layers were washed with brine (10 mL), dried over anhydrous sodium sulfate, filtered and concentrated in vacuo to give crude alcohol (A) (0.27 g). This crude alcohol (A) was passed through a pad of 230-400 mesh silica gel (22.5 g) and eluted with a gradient solvent of ethyl acetate in hexanes (0-12%). The fractions containing the desired compound were evaporated in vacuo to yield pure alcohol (7) (0.096 g, 87.2%). The compound was characterized by spectral data.

Step 2: Deprotection of Protected Alcohol

To a solution of TBDMS protected ether (2.67 g) in methanol (50 mL) was added 10% aqueous HCl (10.00 mL) at room temperature. The reaction mixture was stirred at ambient temperature until completion of reaction. After −1 h the reaction mixture was checked by TLC for its completion. At this stage, the reaction mixture was neutralized with saturated sodium bicarbonate 10 mL) to pH 7-8 and concentrated in vacuo to remove methanol. The reaction mixture was diluted with water 10 mL) and the mixture was then extracted with ethyl acetate (3×30 mL). The combined ethyl acetate extracts were washed with brine (15 mL), dried ($Na_2SO_4$), filtered and concentrated in vacuo to give beraprost ester (A) as a crude, pale-yellow, viscous liquid (2.31 g). The crude product was purified by column chromatography using a gradient solvent of ethyl acetate in hexanes (0-90%). The fractions containing the desired compound were evaporated in vacuo to yield beraprost ester (A) (1.26 g) which was crystallized using a ethyl acetate and cyclopentane mixture to obtain ester with a chiral purity of 96.24% (by HPLC); mp 82-83° C. (dec.); Required: C=72.79; H=7.82; Found C=72.86; H=7.41. The compound was characterized by spectral data.

Option 2: Deprotection/Reduction

Step 1: Deprotection of Protected Alcohol

To a solution of enone (0.450 g) in methanol (10 mL) was added 10% aqueous HCl (0.90 mL) at ambient temperature. The reaction mixture was stirred at ambient temperature until completion of reaction. After ~3 h the reaction mixture was checked by TLC for its completion. At this stage, the reaction mixture was neutralized with saturated sodium bicarbonate to pH 7-8 and concentrated in vacuo to remove methanol. The reaction mass was diluted with water (10 mL) and the mixture was extracted with ethyl acetate (2×15 mL). The combined ethyl acetate extracts were washed with brine (10 mL), dried ($Na_2SO_4$), filtered and concentrated in vacuo to give the keto alcohol as a crude, pale-yellow, viscous liquid (0.400 g). The crude product was crystallized using a ethyl acetate and hexanes mixture to obtain pure, crystalline keto-alcohol (0.210 g, 60%); mp 75-76° C.; The compound was characterized by spectral data.

Step 2: Selective Reduction

A 100 mL, three-necked, round-bottom flask equipped with a magnetic stir bar, a thermocouple, and an argon inlet-outlet adapter was charged with keto-alcohol (8) (3.25 g) and anhydrous toluene (100 mL). A solution of (R)-(+)-2-butyl CBS oxazaborolidine (1.0 M in toluene) (23.8 mL) was added under argon at room temperature. The mixture was cooled to −15° C. (dry ice/acetone-bath), and catecholborane (23.8 mL) was added slowly maintaining the temperature between −15° C. and −10° C. After complete addition, the reaction mixture was stirred for 1-2 h while slowly allowing the temperature to raise to ambient temperature. The progress of the reaction was monitored by TLC. The reaction mixture was carefully quenched by slow addition of methanol (50 mL) over a period of 10 minutes maintaining the temperature between −15° C. and −10° C. The reaction mixture was allowed to warm to room temperature and the stirring was continued for another 20-30 minutes. At this stage, saturated aqueous ammonium chloride solution (10 ml) was added with stirring. The organic layer was separated, and the aqueous layer was extracted with ethyl acetate (3×50 mL). The combined organic layers were washed with brine (15 mL), dried over anhydrous sodium sulfate, filtered and concentrated in vacuo to give crude beraprost ester (A). The crude product was purified by column chromatography using a gradient solvent of ethyl acetate in hexanes (0-90%). The fractions containing the desired compound were evaporated in vacuo to yield beraprost ester (A) (2.53 g, 77%). A small sample was crystallized using an ethyl acetate and hexanes mixture to obtain analytically pure beraprost ester diol mp 75-76° C. The compound was characterized by spectral data.

Example 5

Compound A to Beraprost 314d to a Salt

Synthesis of Beraprost 314d

To a solution of beraprost ester (A) (0.700 g) in methanol (10 mL) was added a solution of sodium hydroxide (0.815 g in 2.0 mL water) at room temperature. The reaction mixture was stirred at room temperature for ~16 h and the progress of the reaction was monitored by TLC. The reaction mixture was concentrated in vacuo to remove methanol and diluted with water (10 mL). This mixture was acidified with 10% hydrochloric acid solution to pH 2-3. The mixture was extracted with ethyl acetate (2×10 mL). The combined ethyl acetate extracts were washed with brine (1×10 mL), dried ($Na_2SO_4$), filtered and concentrated in vacuo to give the desired stereoisomer of beraprost (314d) as foamy solid (0.700 g). This acid was used out as such for potassium salt formation Synthesis of Potassium Salt of Beraprost (314d)

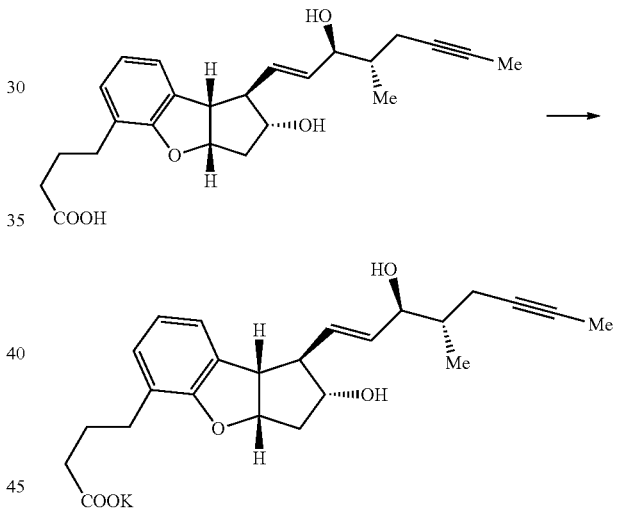

A 100-mL, two-necked, round-bottom flask equipped with a magnetic stirrer and a thermometer was charged with beraprost (314d) (0.500 g) and ethyl acetate (15 mL). This mixture was warmed to 75-80° C. to obtain a clear solution. To this clear solution, potassium hydroxide (0.066 g) in ethanol (3.0 mL) was added and stirred for few minutes at 75-80° C., then the mixture was allowed to cool to ambient temperature over a period of approximately 2 h. At ambient temperature, the precipitated product was isolated by filtration and washed with ethanol. The product was transferred from Buchner funnel to a glass dish for air-drying overnight in a fume hood to yield free flowing white-solid salt of beraprost (0.420 g); the solid was crystallized from ethanol and water to obtain pure stereoisomer of beraprost potassium salt, chiral purity 99.6% by Chiral HPLC; mp 270-272° C. (dec.); Required: C=66.03; H=6.70; Found C=65.82; H=6.67. The compound was characterized by spectral data.

Example 6

Synthesis of Side Chain With Chiral Methyl

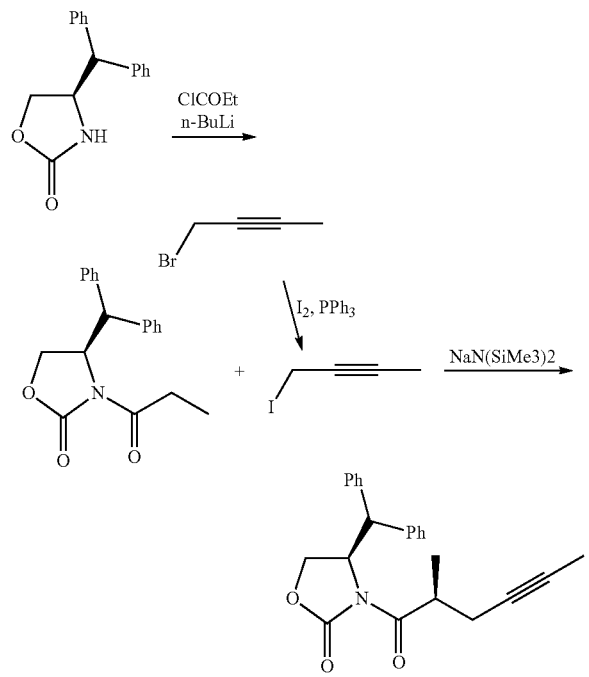

Step 1:

A 2-L, three-necked, round-bottom flask equipped with a mechanical stirrer and an argon inlet-outlet adapter connected to a bubbler was charged with a solution of (R)-(+)-4-(diphenylmethyl)2-oxazolidinone (2, 25 g in 200 mL of THF). The solution was cooled to −78° C. under argon. To the solution was added n-butyllithium in hexanes (1.6 M, 64.80 mL) drop wise at −78° C. over a period of 45-60 minutes. The reaction mixture was stirred at −78° C. for 30-45 min. Then, propionyl chloride (20.10 g dissolved in 30-50 mL of dry THF) was added drop wise at −78° C. over 15-30 min. The mixture was stirred at −78° C. for 1-2 h (Note 1). The reaction mixture was quenched with saturated solution of ammonium chloride (15 mL) at −78° C. to −60° C. and then allowed to warm-up to ambient temperature. An additional amount of ammonium chloride (100 mL) was added to the reaction mixture at ambient temperature and the mixture was swirled in separatory funnel. The organic layer was separated from aqueous layer. The aqueous phase was extracted with MTBE (2×100 mL). The combined organic phases were washed with aqueous NaHCO$_3$ (100 mL), brine (100 mL), then dried over anhydrous Na$_2$SO$_4$ followed by filtration. The filtrate was concentrated in vacuo to afford crude solid product (30.38 g, quantitative).

Step 2:

A 500-mL, round-bottom flask equipped with a magnetic stirrer and an argon inlet-outlet adapter connected to a bubbler was charged with 1-bromo-2-butyne (23.21 g) and THF (100-120 mL) under argon at room temperature. To the solution of 1-bromo-2-butyne, sodium iodide (27.90 g) was added. The reaction mixture was stirred for 2-3 h at ambient temperature. The suspension was filtered using a Whatmann filter paper No. 50 and the solid washed with dry THF (15-30 mL). The filtrate containing 1-iodo-2-butyne in THF was used in the next step.

Step 3:

A 2-L, three-necked, round-bottom flask equipped with a mechanical stirrer and an argon inlet-outlet adapter connected to a bubbler was charged with a solution of NaN(SiMe$_3$)$_2$ (1.0 M, 174 mL). To this solution was added a solution of oxazolidinone (36 g in 50-80 mL of THF) drop wise at −78° C. After the mixture was stirred at −78° C. for 60-120 min, 1-iodo-2-butyne (freshly prepared in THF in step one) was added drop wise at −78° C. over a period of 45-60 min using a dropping funnel. The mixture was stirred for 2 h, and then quenched the reaction mixture with acetic acid (11 mL) at −78° C. The mixture was allowed to warm to ambient temperature and aqueous sodium chloride (500-750 mL) was added. The organic layer was separated from the aqueous layer. The aqueous phase was extracted with MTBE (3×400 mL). The combined organic phases were washed with aqueous NaHCO$_3$ (100 mL), then dried over anhydrous Na$_2$SO$_4$, followed by filtration. The filtrate was concentrated in vacuo to ⅕th of the total volume. Ethanol (150 mL) was added and the mixture concentrated in vacuo to a slurry. An additional amount of ethanol (200 mL) was added and then concentrated again in vacuo to a slurry in order to remove other solvents carried over from reaction and work-up.

Crystallization:

To the resulting slurry, ethanol 300-350 mL was added and mixture was heated to obtain a clear solution. The clear solution was allowed to cool slowly to ambient temperature. The resulting solid was collected by filtration and washed with a solution of ethanol in hexanes (50%, 50-150 mL). The solid product was transferred to glass tray and air-dried to afford white, crystalline oxazolidinone (24.74 g, 59%), mp 128-130° C.

Example 7

Synthesis of Phosphonate Side Chain

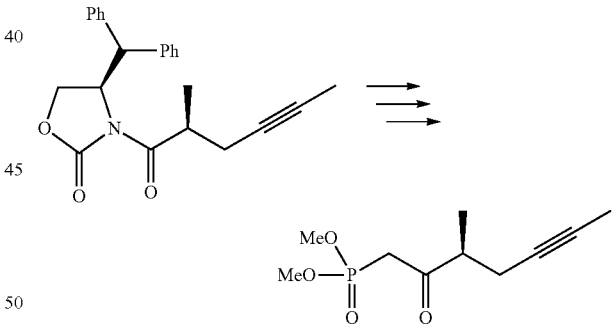

Step 1:

A 500-mL, round-bottom flask equipped with a mechanical stirrer was charged with a solution of oxazolidinone 8 (24.50 g) in THF (295 mL), water (114 mL) and LiOH (2.273 g). The mixture was stirred at ambient temperature for 16-24 h. A saturated solution of sodium bicarbonate (50-75 mL) was added to the reaction mixture slowly while stirring. The reaction mixture was extracted with MTBE (5×100 mL) to remove the chiral auxiliary and impurities. The aqueous layer was adjusted to pH 3-4 by addition of dilute hydrochloric acid and extracted with MTBE (3×150 mL). The combined organic layers were washed with brine (1×150 mL), and then dried over anhydrous Na$_2$SO$_4$, followed by filtration. The filtrate was concentrated in vacuo to give crude carboxylic acid (6.4 g, 74.5%).

Step 2:

A 500-mL, round-bottom flask equipped with a magnetic stirrer was charged with carboxylic acid (10) (6.35 g), 2-chloro-4,6-dimethoxy-1,3,5-triazine (11.93 g), and N-methylmorpholine (14.6 mL) in THF (70-100 mL). The suspension was stirred at ambient temperature for 1-2 h. After stirring for 1-2 h, MeO(Me)NH.HCl (5.89 g) was added and the mixture stirred at RT overnight (16-18 h). To the reaction mixture, hexane (50-100 mL) was added. The slurry was filtered through a pad of Celite. The Celite bed was washed with hexanes (50-100 mL). The filtrate was concentrated in vacuo to afford crude amide (11). The crude product was dissolved in hexane (50-100 mL) and filtered again through a pad of Celite in order to remove suspended solid impurities. The Celite bed was washed with hexanes (50-100 mL). The filtrate was concentrated in vacuo to afford crude product. The crude product was purified by silica gel column chromatography (gradient: EtOAc/hexanes, 5-25%) to afford Weinreb amide (7.2 g, 85%) as a colorless oil with a 98.42% purity (by chiral HPLC).

Step 3:

A 500-mL, three-necked, round-bottom flask equipped with a magnetic stirrer and an argon inlet-outlet adapter connected to a bubbler was charged with a solution of dimethyl methylphosphonate (A) (13.00 g) in THF (50 mL) followed by drop wise addition of n-BuLi (1.6 M in hexanes, 52.50 mL) at −78° C. using a dropping funnel. The mixture was stirred at −78° C. for 1 h and then a solution of amide 11 (7.10 g) in THF (20-30 mL) was added over a period of 30-45 minutes using a dropping funnel. After complete addition, the mixture was stirred at −78° C. for 2 h, then the reaction was quenched with aqueous $NH_4Cl$ (100 mL). The mixture was allowed to warm-up to ambient temperature. The mixture was extracted with ethyl acetate (3×75 mL). The combined organic layers were washed with brine (1×50 mL), then dried over anhydrous $Na_2SO_4$, followed by the filtration. The filtrate was concentrated in vacuo to afford crude product. The crude product was purified by column chromatography (gradient, EtOAc/hexanes, 10-100%) to afford (S)-3-methyl-2-oxohept-5-ynylphosphonic acid dimethyl ester (9.218 g, 95%).

All of the publications, patent applications and patents cited in this specification are incorporated herein by reference in their entirety.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

What is claimed is:

1. A process for preparing a substantially pure compound of the following formula:

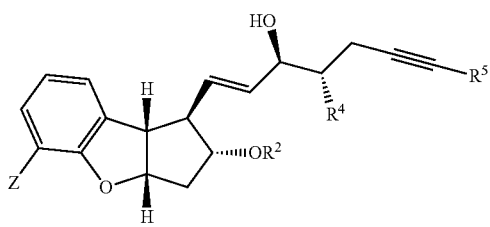

$R^2$ represents H or a hydroxy protective group,
$R^4$ represents H or $C_{1-3}$ alkyl,
$R^5$ represents H or $C_{1-6}$ alkyl, and
Z represents $C_{1-12}$ alkyl-$COOR^{12}$, $R^{12}$ is a cation, H, or $C_{1-12}$ alkyl, comprising the steps of:

(1) reacting an aldehyde of the formula

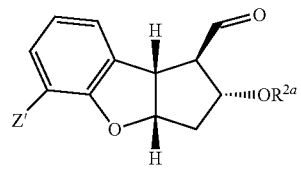

with a substantially pure compound of the formula:

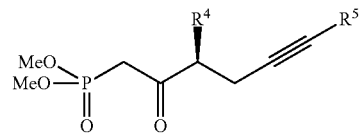

wherein Z' is $C_{1-12}$ alkyl-$COOR^{12'}$, $R^{12'}$ is a $C_{1-6}$ alkyl or a protecting group, $R^{2a}$ is a hydroxy protecting group, $R^4$ and $R^5$ are each defined above to form a compound of the following formula:

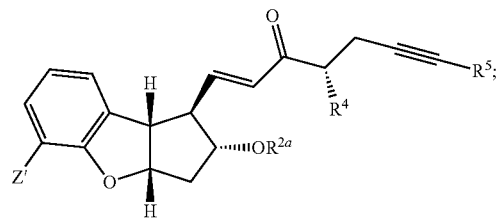

and (2) selectively reducing the carbonyl and deprotecting secondary alcohol to form a substantially pure compound of the following formula:

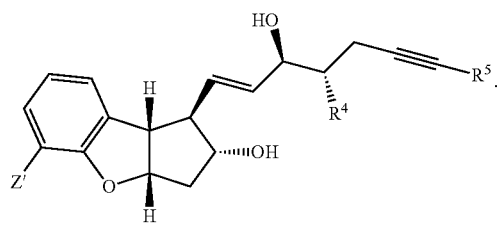

2. The method of claim 1, wherein selective reduction of the carbonyl includes an asymmetric catalyst.

3. The method of claim 1, further comprising deprotecting the ester of protected acid of Z' to form an acid or salt thereof.

4. The method of claim 3, wherein $R^4$ and $R^5$ are each $CH_3$, Z is $(CH_2)_3COO$ $R^{12}$ and $R^{12}$ is a cation or H.

5. The method of claim 4, wherein $R^{12}$ is a cation and the cation is $K^+$.

6. The method of claim 5, wherein the resulting substantially pure compound comprises greater than 99% of the isomer represented by the following formula:

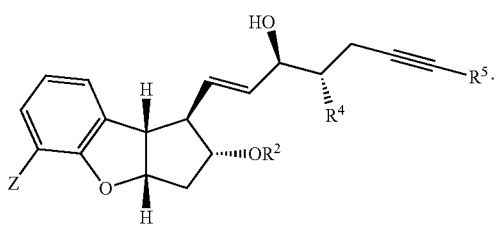

7. The method of claim 3, wherein Z' is $C_{1-12}$ alkyl-$COOR^{12'}$, and $R^{12'}$ is a $C_{1-6}$ alkyl.

8. The method of claim 1, wherein $R^{2a}$ is a silyl protecting group.

9. The method of claim 8, wherein $R^{2a}$ is trimethylsilyl, triethylsilyl, t-butyldimethylsilyl, t-butyldiphenylsilyl or phenyldimethylsilyl.

10. The method of claim 1, wherein said selective reducing uses a selective reducing agent selected from the group consisting of (R)-(+)-2-Butyl-CBS-oxazaborolidine and catecholborane, (R)-(+)-2-Methyl-CBS-oxazaborolidine and catecholborane, (+) DIP-chloride, $NaBH_4$ and 2-(3-Nitrophenyl)-1,3,2-dioxaborolane-4S,5S-dicarboxylic acid (D-TarB-$NO_2$), modified DIBAL reagents, and modified LAH agents.

11. The method of claim 1, wherein $R^{2a}$ is a silyl protecting group and wherein said selective reducing uses a selective reducing agent selected from the group consisting of (R)-(+)-2-Butyl-CBS-oxazaborolidine and catecholborane, (R)-(+)-2-Methyl-CBS-oxazaborolidine and catecholborane, (+) DIP-chloride, $NaBH_4$ and 2-(3-Nitrophenyl)-1,3,2-dioxaborolane-4S,5S-dicarboxylic acid (D-TarB-$NO_2$), modified DIBAL reagents, and modified LAH agents.

12. The method of claim 11, wherein $R^{2a}$ is trimethylsilyl, triethylsilyl, t-butyldimethylsilyl, t-butyldiphenylsilyl or phenyldimethylsilyl.

* * * * *